US007906324B2

(12) United States Patent
Anderson et al.

(10) Patent No.: US 7,906,324 B2

(45) Date of Patent: Mar. 15, 2011

(54) APPARATUS AND METHOD FOR INCUBATING CELL CULTURES

(75) Inventors: James Anderson, Huntsville, AL (US); Amy Bishop, Huntsville, AL (US)

(73) Assignee: The Board of Trustees of the University of Alabama, Huntsville, AL (US)

( * ) Notice: Subject to any disclaimer, the term of this patent is extended or adjusted under 35 U.S.C. 154(b) by 1212 days.

(21) Appl. No.: 11/433,375

(22) Filed: May 12, 2006

(65) Prior Publication Data

US 2006/0275896 A1 Dec. 7, 2006

Related U.S. Application Data

(60) Provisional application No. 60/680,195, filed on May 12, 2005.

(51) Int. Cl.

| | |
|---|---|
| *C12M 1/00* | (2006.01) |
| *C12M 3/00* | (2006.01) |
| *C12M 1/36* | (2006.01) |
| *C12M 1/38* | (2006.01) |
| *C12M 1/12* | (2006.01) |
| *C12M 1/21* | (2006.01) |

(52) U.S. Cl. ............... 435/303.1; 435/283.1; 435/286.5; 435/297.2; 435/301.1

(58) Field of Classification Search .................... 289/10; 435/283.1, 286.5, 297.2, 301.1, 303.1

See application file for complete search history.

(56) References Cited

U.S. PATENT DOCUMENTS

| | | | |
|---|---|---|---|
| 3,591,461 A | 7/1971 | Bazil et al. | |
| 3,941,662 A | 3/1976 | Munder et al. | |
| 3,948,732 A | 4/1976 | Haddad et al. | |
| 4,514,499 A | 4/1985 | Noll | |
| 4,537,860 A | 8/1985 | Tolbert et al. | |
| 4,839,292 A | 6/1989 | Cremonese | |
| 5,330,915 A * | 7/1994 | Wilson et al. | 435/286.6 |
| 5,424,209 A | 6/1995 | Kearney | |

(Continued)

OTHER PUBLICATIONS

Abstract of Japanese Patent Application No. JP2001225475, entitled, "Liquid Ejection Head, Its Manufacturing Method, and Liquid Ejector," Canon KK, Aug. 21, 2001.

(Continued)

*Primary Examiner* — Walter D Griffin

*Assistant Examiner* — Lydia Edwards

(74) *Attorney, Agent, or Firm* — Lanier Ford Shaver & Payne, P.C.; Jon E. Holland

(57) ABSTRACT

A portable, self-contained incubation apparatus has a cell container in which a cell culture can grow. The cell container resides on a base along with other components that maintain the environmental conditions inside of the container within a desired range. The self-contained incubation apparatus is portable allowing the conditions within the cell container to be precisely controlled even as it is being moved from one location to another. Further, at least one transparent surface of the cell container enables observation of the cell culture. Thus, the culture can be observed while the environmental conditions within the container are being controlled by components of the incubation apparatus. Since the cells can be observed without breaking the air-tight seal of the container, observation of the cells can be performed as often as is desired without introducing contaminants to the culture or otherwise significantly affecting the growth environment within the container. Indeed, observation of the cells can be performed as often as is desired without introducing contaminants to the culture or otherwise significantly affecting the growth environment within the container.

23 Claims, 12 Drawing Sheets

U.S. PATENT DOCUMENTS

| | | | |
|---|---|---|---|
| 5,736,398 | A | 4/1998 | Giambernardi et al. |
| 5,747,333 | A | 5/1998 | Jungmann-Campello et al. |
| 5,801,055 | A | 9/1998 | Henderson |
| 5,817,509 | A | 10/1998 | Stevens et al. |
| 5,858,770 | A | 1/1999 | Perlman |
| 5,863,792 | A | 1/1999 | Tyndorf et al. |
| 5,888,807 | A * | 3/1999 | Palsson et al. ............. 435/293.2 |
| 5,985,653 | A | 11/1999 | Armstrong et al. |
| 6,218,178 | B1 | 4/2001 | Banes |
| 6,271,027 | B1 | 8/2001 | Sarem et al. |
| 6,329,195 | B1 | 12/2001 | Pfaller |
| 6,455,310 | B1 | 9/2002 | Barbera-Guillem |
| 6,479,252 | B1 | 11/2002 | Barbera-Guillem |
| 6,521,451 | B2 | 2/2003 | Potter |
| 6,562,616 | B1 | 5/2003 | Toner et al. |
| 6,576,458 | B1 | 6/2003 | Sarem et al. |
| 6,627,435 | B2 | 9/2003 | Chan et al. |
| 6,670,169 | B1 | 12/2003 | Schob et al. |
| 6,730,510 | B2 | 5/2004 | Roos et al. |
| 6,821,772 | B2 | 11/2004 | Barbera-Guillem et al. |
| 7,507,579 | B2 * | 3/2009 | Boccazzi et al. ........... 435/297.5 |
| 2001/0039045 | A1 | 11/2001 | Chan et al. |
| 2003/0092178 | A1 * | 5/2003 | Yerden .......................... 435/375 |
| 2004/0126876 | A1 | 7/2004 | Ravin et al. |
| 2004/0229348 | A1 | 11/2004 | Kahlert et al. |

OTHER PUBLICATIONS

Abstract of Japanese Patent Application No. JP2003164165, entitled, “Circuit Device,” Semikron Elektron GMBH, Jun. 6, 2003.

Abstract of Japanese Patent Application No. JP2003272681, entitled, “Fuel Cell System,” Nissan Motor, Sep. 26, 2003.

* cited by examiner (Top View)

(Bottom View)

48
37
51
49
51
35
38
39
34
32
33
36
51
75
51
52
69
87
55
31
81
MIXER
20
77
22
133

(Side View)

(Bottom View)

(Top View)

(Top View)

APPARATUS AND METHOD FOR INCUBATING CELL CULTURES

CROSS REFERENCE TO RELATED APPLICATION

This application claims priority to U.S. Provisional Application No. 60/680,195, entitled "Cell Culture Support System," and filed on May 12, 2005, which is incorporated herein by reference.

RELATED ART

Typical cell culture techniques for any cell type, e.g., mammalian, plant, or insect, utilize an expensive and bulky outlay of equipment and resources. Cells can be grown in a vast array of vessels, which are usually kept in a chamber of an incubator. The incubator maintains the conditions, such as temperature, humidity, acidity, etc., of the chamber within a desired range to enhance cell growth.

Although an incubator can improve cell growth for the vessels contained therein, efforts to monitor the cells during growth can be significantly hampered. In this regard, a culture within a vessel, such as a Petri dish, is typically observed by removing the vessel from the incubator and viewing the culture under a microscope. After observing the culture, the vessel can be returned to the incubator for further cell growth. When the vessel is outside of the incubator, the environmental conditions of the vessel are no longer controlled by the incubator and can vary depending on room conditions thereby impairing cell growth. Generally, the longer the vessel remains outside of the incubator, the greater is the impact to cell growth. Thus, the number and durations of observation periods are typically limited in an effort to reduce adverse effects to cell growth. Unfortunately, limiting the number and durations of observation periods also limits the amount of data that can typically be collected on the culture.

In addition, removing a vessel from the incubator exposes the vessel to room conditions increasing the likelihood of contamination to the culture. Further, opening the incubator to remove or return any vessel can contaminate the environment within the incubator potentially affecting any of the vessels situated therein. Opening and closing of the incubator can also adversely affect the temperature, humidity, acidity, and other environmental conditions that the incubator is attempting to maintain. Opening and closing the vessel itself can result in contamination and disruption of the environment within the vessel. The vessel typically needs to be opened to feed the cells within the vessel.

Moreover, improved incubation devices and systems are generally desired so that the environmental conditions for a cell culture can be better maintained and contamination of the cell culture can be reduced. It also would be desirable for an incubating system to allow for better observation of the cell culture, including longer observation times, without significantly affecting the environmental conditions in which the cell culture is located.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally relates to devices and methods for incubating cell cultures. In one embodiment of the present disclosure, a self-contained incubation apparatus has a cell container in which a cell culture can grow. The cell container resides on a base with other components that maintain the environmental conditions inside of the container within a desired range. The self-contained incubation apparatus is portable allowing conditions within the cell container to be precisely controlled even as it is being moved from one location to another. Further, at least one transparent surface of the cell container enables observation of the cell culture. Thus, the culture can be observed while the environmental conditions within the container are being controlled by components of the incubation apparatus. Indeed, observation of the cells can be performed as often as is desired without introducing contaminants to the culture or otherwise significantly affecting the growth environment within the container.

Figure 1:
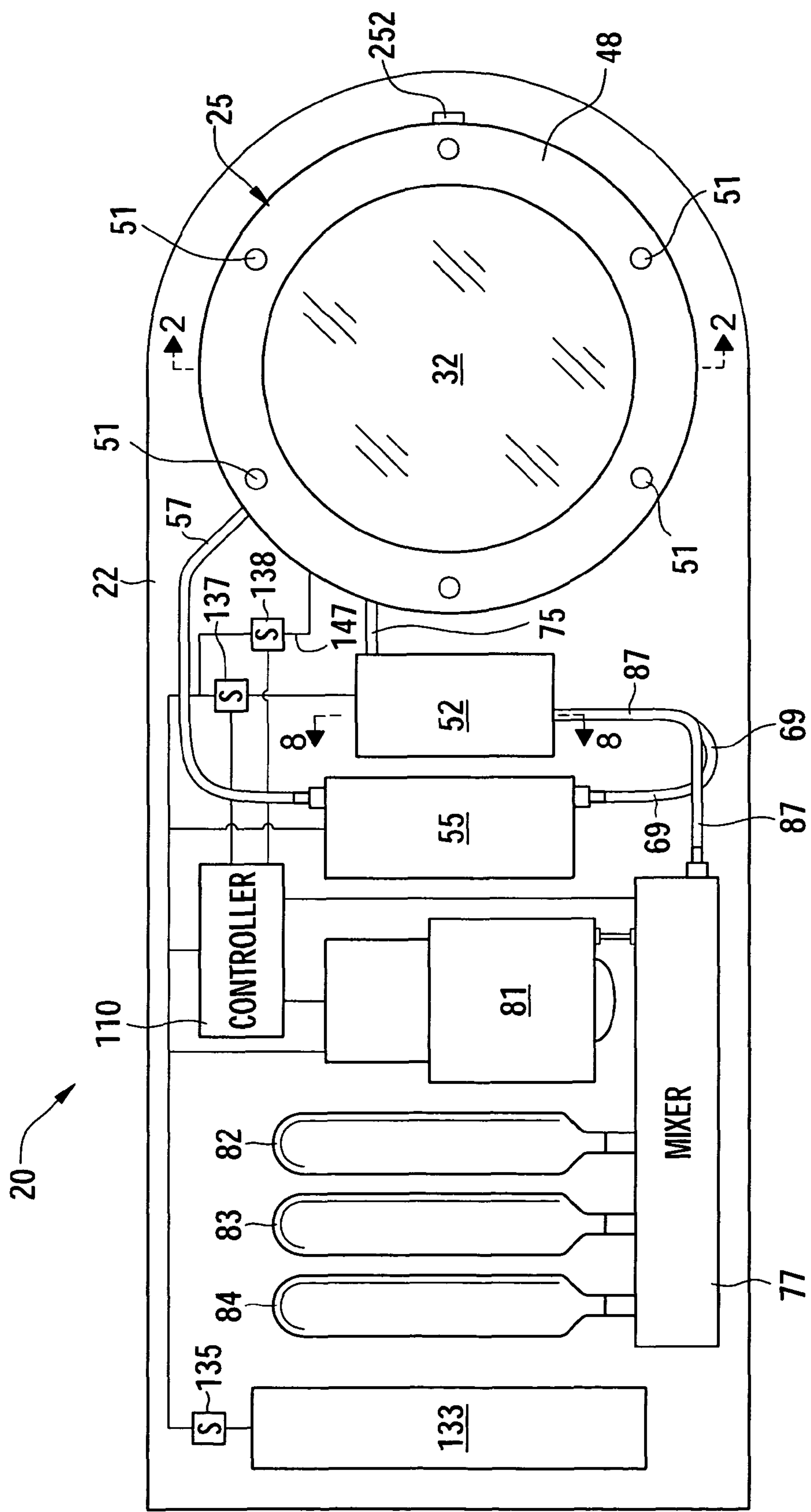
FIG. 1 illustrates a top view of a self-contained incubation apparatus in accordance with an exemplary embodiment of the present disclosure.

FIG. 1 depicts a self-contained incubation apparatus 20 in accordance with one exemplary embodiment of the present disclosure. As shown by FIG. 1, the apparatus 20 has a base 22 on which various components are mounted. As an example, the base 22 may be implemented via a printed circuit board (PCB) that provides electrical connectivity between various components of the apparatus 20, as will be described in more detail hereafter. The base 22 may have different shapes and forms in different embodiments and may comprises various interconnected segments. For example, the base may comprise a plurality of interconnected PCBs or other types of boards instead of the single PCB shown by FIG. 1.

Figure 2:
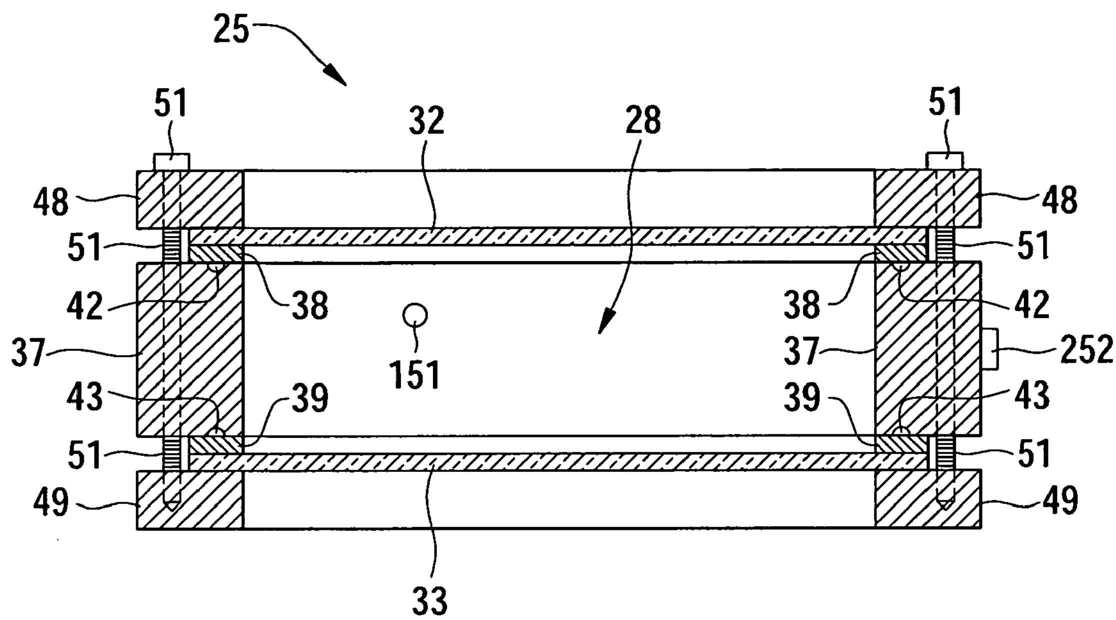
FIG. 2 is a cross-sectional view of a cell container depicted in FIG. 1.

A cell container 25 is mounted on the base 22. As shown by FIG. 2, the container 25 defines a chamber 28 in which a cell culture, e.g., mammalian, plant, or insect, may be placed for growth. Media, such as Dulbecco's Modified Eagle Media (DMEM), may be injected into the chamber 28 to promote growth of the culture. In the embodiment depicted by FIGS. 1 and 2, the container 25 is circular and has a diameter of about 3 inches, but other types of shapes and dimensions may be used in other embodiments.

Figure 3:
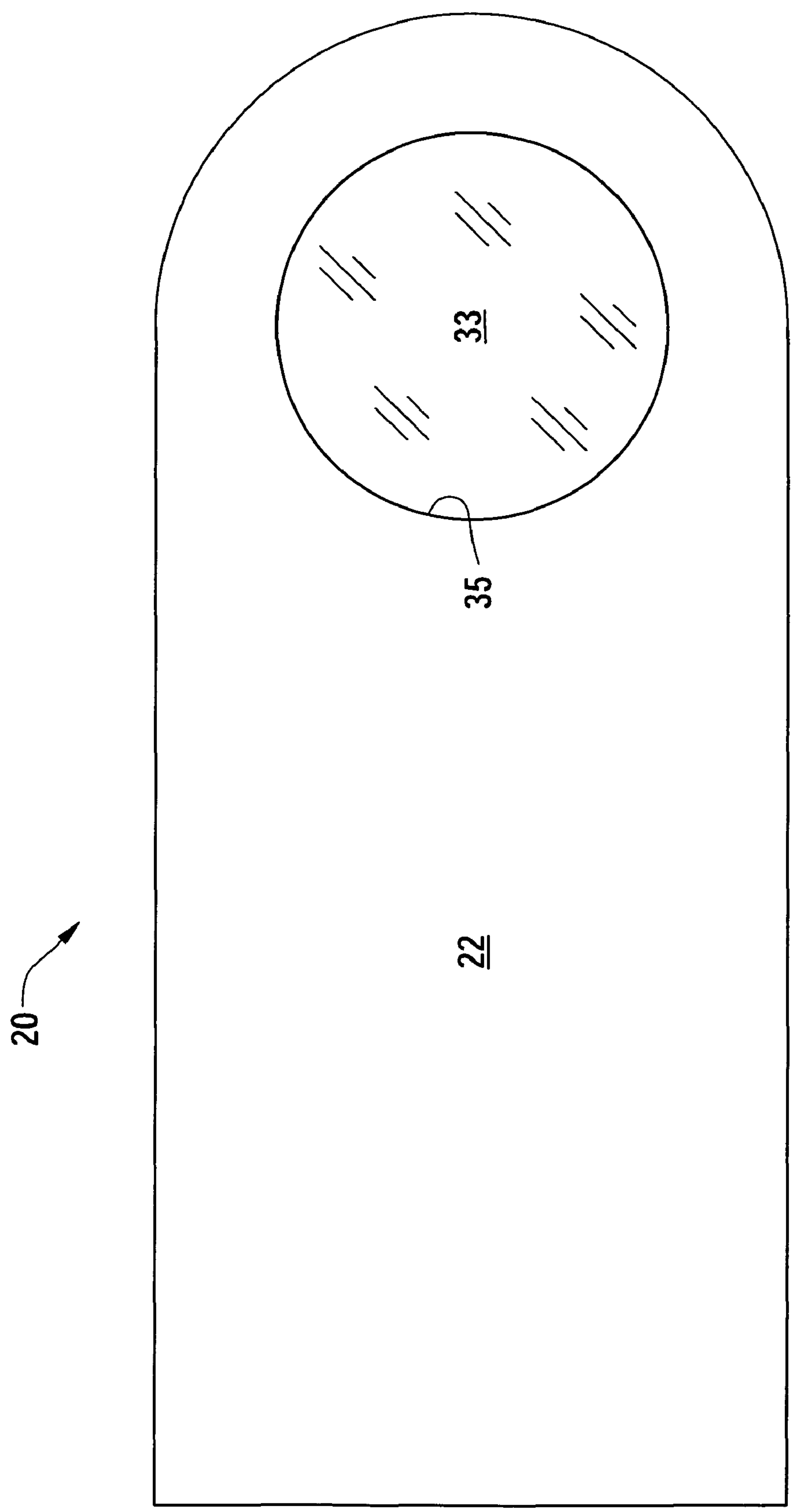
FIG. 3 is a bottom view of the incubation apparatus depicted in FIG. 1.

Referring to FIG. 2, the container 25 has an upper plate 32 and a lower plate 33, which are both transparent. In this regard, the upper and lower plates 32 and 33 may be composed of glass, polystyrene, or some other transparent material. Further, as shown by FIG. 3, the base 22 has a hole 35, which exposes the lower plate 33. The culture within the container 25 can be viewed through the transparent upper plate 32 and/or lower plate 33.

Figure 4:
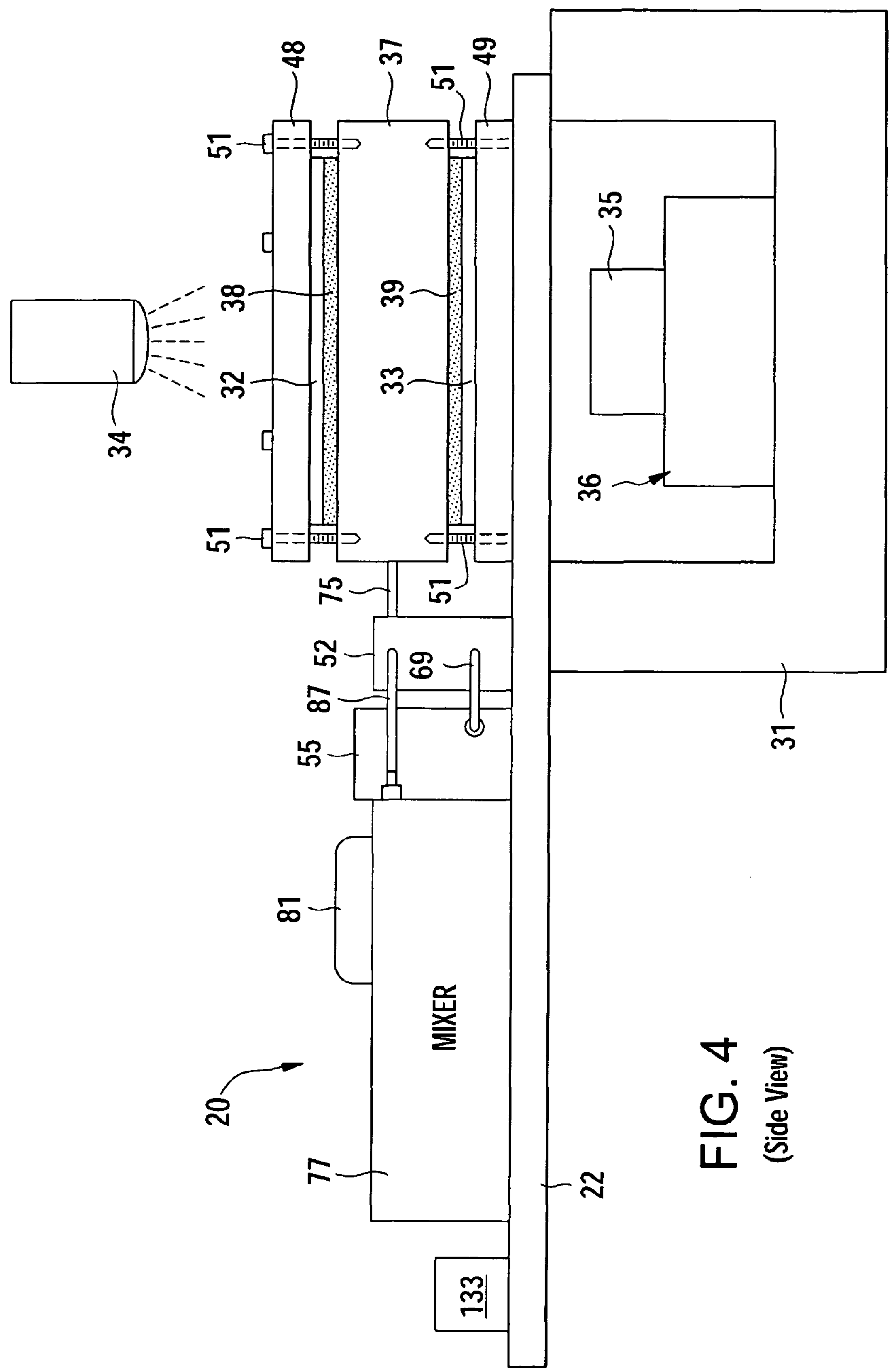
FIG. 4 is a side view of the incubation apparatus of FIG. 1 when this apparatus is placed on a light source underneath a microscope.

As an example, a microscope lens can be positioned adjacent either plate 32 or 33 and used to view the culture that is within the chamber 28. Indeed, in one embodiment depicted in FIG. 4, a light source 34 is positioned adjacent to the upper plate 32 so that light from the light source 34 passes through the upper plate 32 and into the chamber 28. Further, a lens 35 of a microscope 36 is positioned adjacent the other plate 33 so that the culture can be viewed via the microscope 36 through the lower plate 33. In this regard, light from the light source 34 illuminates the culture for viewing via the microscope 36. In the embodiment depicted by FIG. 4, the microscope 36 is mounted on a frame 31 on which the apparatus 20 is placed. In other examples, it is possible for the light source 34 to be positioned adjacent the upper plate 32 and for the microscope lens 35 to be placed adjacent the lower plate 33. Any conventional microscope, including standard and inverted microscopes, may be used to observe the culture in the container 25 via plate 32 or 33.

In the embodiment depicted by FIGS. 1 and 2, each of the plates 32 and 33 has a circular shape, although other shapes for either of the plates 32 or 33 are possible in other embodiments. Further, the total diameter of the upper plate 32 is about 2¾ inches (in.), and the exposed portion of the upper plate 32 has a diameter of about 1 15/16 inches. Similarly, the total diameter of the lower plate 33 is about 2¾ inches, and the exposed portion of the lower plate 33 has a diameter of about 1 15/16 inches. In other embodiments, other sizes of the plates 32 and/or 33, as well as the exposed portions of these plates 32 and/or 33, are possible.

As shown by FIG. 2, the upper and lower plates 32 and 33 are separated by a support member 37, an upper gasket 38, and a lower gasket 39. In the exemplary embodiment depicted by FIG. 2, each of the support member 37, the upper gasket 38, and the lower gasket 39 is shaped as a circular ring, although other shapes are possible in other embodiments for any of these components. The support member 37 has an upper channel 42, which is used to pass media out of the chamber 38, as will be described in more detail hereafter. The support member 37 also has a lower channel 43, which is used to pass media into the chamber 38, as will be described in more detail hereafter.

An upper support member 48 is positioned on the upper plate 32, and a lower support member 49 is positioned on the lower plate 33. Screws 51 are screwed through the support members 37, 48, and 49 in order to hold the components of the container 25 in a fixed relationship with each other. In this regard, the lower support member 49 can be pressed against the lower plate 33, and the upper support member 48 can be pressed against the upper plate 32. While in this arrangement, the screws 51 can be inserted. Frictional forces caused by the components being pressed against each other then hold the upper plate 32 and gasket 38 between members 37 and 48, and these frictional forces also hold the lower plate 33 and gasket 39 between members 37 and 49. Moreover, the inner walls of the support member 37, the gaskets 38 and 39, the upper plate 32, and the lower plate 33 define the chamber 28.

If an air tight seal for the chamber 28 can be formed without the use of gaskets 38 and 39, then the gaskets 38 and 39 may be unnecessary. For example, in other exemplary embodiments, the upper plate 32 and lower plate 33 may be integrated with the support member 37 thereby forming an air-tight seal for the chamber 28 without the use of gaskets 38 and 39.

As shown by FIG. 1, a reservoir 52 and a pump 55 are mounted on the base 22. The reservoir 52 holds media that is pumped out of the chamber 28. In this regard, the pump 55 draws media out of the chamber 28 through the upper channel 42 (FIG. 2) and a hose 57 (FIG. 1), which connects the container 25 to the pump 55. The media passes through the pump 55 and into a hose 69, which connects the pump 55 to the reservoir 52. The media passing through the pump 55 is received by the reservoir 52. The media entering the reservoir 52 forces media already in the reservoir 52 out through a hose 75 that connects the reservoir 52 to the container 25. The media passing through the hose 75 enters chamber 28 through the lower channel 43 (FIG. 2).

Note that the container 25 is preferably gas-tight except for the channels 42 and 43 that extend to hoses 57 and 75, respectively. Thus, no gases can be introduced to the chamber 28 except through the reservoir 52, as will be described in more detail hereafter.

Referring to FIG. 1, a mixer 77 is also mounted on the base 22. The mixer 77 delivers gas from at least one gas source. In one exemplary embodiment, an air pump 81 and a container 82 of a particular gas, such as carbon dioxide, are mounted on the base 22. The air pump 81 draws air from the surrounding environment and pumps the air into the mixer 77. Gas from the container 82 is also delivered to the mixer 77. Containers 83 and 84 for additional gases may also be mounted on the base 22 and used to provide other types of gases to the mixer 77. Any number of gas sources, such as pump 81 and containers 82-84, are possible in other embodiments.

The mixer 77 provides gas from at least one of the sources 81-84 depending on the desired gas exchange that is to occur in the reservoir 52, as will be described in more detail hereafter. For example, the mixer 77 may mix air from pump 81 with gas, such as carbon dioxide and/or other gases, from one or more containers 82-84. The gas provided by the mixer 77 passes through a hose 87 and into the reservoir 52.

Figure 5:
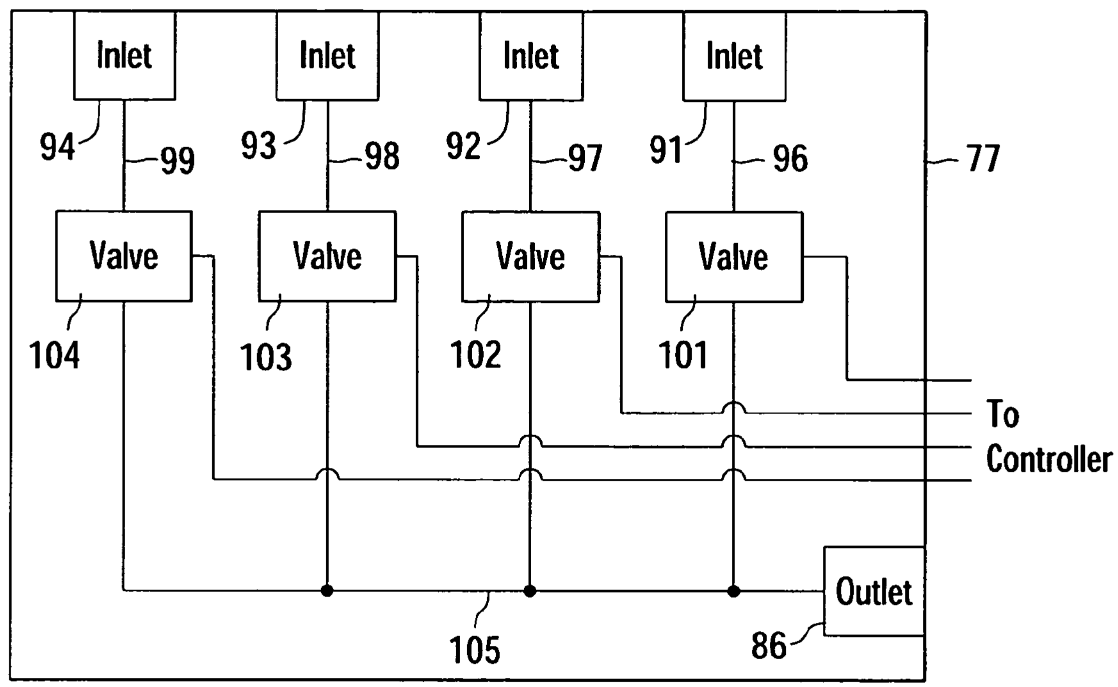
FIG. 5 is a block diagram illustrating an exemplary mixer, such as is depicted in FIG. 1.

FIG. 5 shows a more detailed view of the mixer 77 in accordance with an exemplary embodiment of the present disclosure. As shown by FIG. 5, the mixer 77 has a plurality of inlets 91-94 respectively coupled to the gas sources 81-84 (FIG. 1). In this regard, inlet 91 is coupled to and receives air from the air pump 81, and inlet 92 is coupled to and receives gas from the container 82. Further, inlet 93 is coupled to and receives gas from container 83, and inlet 94 is coupled to and receives gas from container 84.

A plurality of channels 96-99 extend from the inlets 91-94 to a plurality of valves 101-104, respectively, as shown by FIG. 5. Further, a channel 105 extends from each valve 101-104 to an outlet 86. Each valve 101-104, when in an open state, allows gas to flow from its respective inlet 91-94 to the outlet 86. In this regard, the containers 82-84 are pressurized such that gas flows through values 102-104 when opened. When in a closed state, each valve 101-104 prevents gas from flowing therethrough. Thus, when valve 101 is opened, air flows from the pump 81 through valve 101 and channels 96 and 105 to outlet 86. When valve 102 is opened, gas flows from the container 82 through valve 102 and channels 97 and 105 to outlet 86. When valves 103 and 104 are opened, gas flows from the containers 83 and 84, respectively, through channels 98, 99, and 105 to outlet 86. Each valve 101-104 may be implemented via a solenoid valve or some other known or future-developed valve.

Moreover, the valves 101-104 are selectively controlled such that the desired mixture is passed through the outlet 86, which is coupled to each of the valves 101-104. For example, assume that a mixture of 95% air and 5% carbon dioxide is desired and that the container 82 coupled to inlet 92 holds pure carbon dioxide. In such an example, the valve 101 may be placed in an open state for the duration of a given experiment, and the valve 102 may be selectively opened and closed during the experiment such that the mixture passing through outlet 86 corresponds to the desired ratio of air and carbon dioxide.

In one exemplary embodiment, the states of the valves 101-104 are controlled by a controller 110 (FIG. 5) mounted on the base 22. The controller 110 also controls various other components of the apparatus 20, as will be described in more detail hereafter. As an example, the controller 110 may be coupled to the air pump 81 in addition to the mixer 77. When air is to be mixed by the mixer 77, the controller 110 may enable the air pump 81 and open the valve 101 (FIG. 5) such that air is injected into the mixer 77 by the pump 81 and passes through the valve 101 to the outlet 86. If air is not to be mixed by the mixer 77, the controller 110 may close the valve 101 and disable or bypass the pump 81. The controller 110 may also control whether other gases are mixed by the mixer 77 by controlling the states of the valves 102-104.

Operation of the controller 110 is generally controlled by control logic 115 (FIG. 6), which may be implemented in hardware, software or a combination thereof. In the exemplary embodiment illustrated in FIG. 6, the control logic 115, along with its associated methodology, is implemented in software and stored in memory 117 of the controller 110. Note that the control logic 115, when implemented in software, can be stored and transported on any computer-readable medium for use by or in connection with an instruction execution device, such as a processor, that can fetch and execute instructions.

Figure 6:
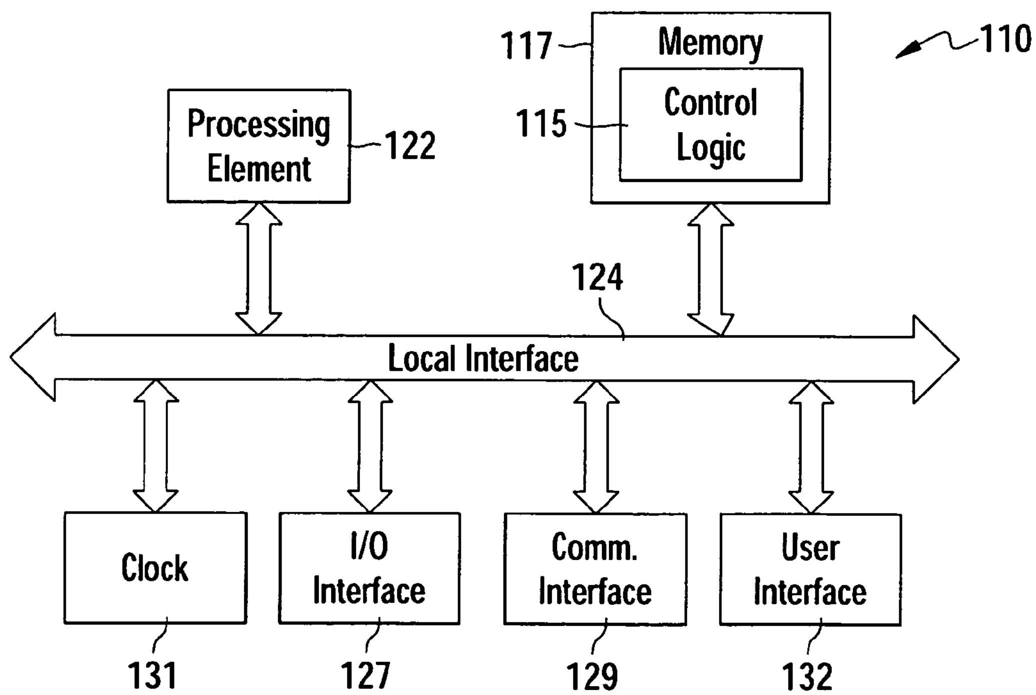
FIG. 6 is a block diagram illustrating an exemplary controller, such as is depicted in FIG. 1.

The exemplary embodiment of the controller 110 depicted by FIG. 6 comprises at least one conventional processing element 122, such as a digital signal processor (DSP) or a central processing unit (CPU), that communicates to and drives the other elements within the controller 110 via a local interface 124, which can include at least one bus. Furthermore, an input/output (I/O) interface 127 allows the control logic 115 to communicate with and/or control other components of the apparatus 20, and a communication interface 129 allows the apparatus 20 to communicate with a user device (not shown). For example, the communication interface 129 may be detachably coupled to a computer (e.g., a lap-top), or other user device, that allows information to be exchanged between a user and the controller 110. In such an embodiment, the communication interface 129 may be implemented via a universal serial bus (USB) interface or other known devices.

As a mere example, the control logic 115 may record various measurements of the environmental conditions within the container 25 via one or more sensors (not shown in FIG. 6) and report these measurements to a user device via communication interface 129. The interface 129 may also be used to download the logic 115 or other software to the controller 110. In addition, the communication interface 129 may receive user inputs for controlling conditions within the container 25, as will be described in more detail hereafter. Note that the communication interface 129 may communicate with the user device via wireless and/or non-wireless signals.

The controller 110 of FIG. 6 also comprises a clock 131 that enables the controller 110 to track time. In addition, the controller 110 also comprises a user interface 132, such as one or more switches or buttons, to allow a user to provide inputs directly to the apparatus 20. For example, a user may provide manual inputs via interface 132 for controlling environmental conditions within the container 25, as will be described in more detail hereafter.

As shown by FIG. 1, the controller 110 may be coupled to and receive power from a power source 133, such as a battery, that is mounted on the base 22. The power source 133 may also be coupled to and provide power to other components of the apparatus 20. For example, the power source 133 may be coupled to and provide power to each of the pumps 55 and 81. In the embodiment shown by FIG. 1, the power source 133 is coupled to the other components through a switch 135 so that power can be selectively applied to the components by controlling the state of the switch 135. Note that it is unnecessary for the power source to reside on the base 22. For example, in other embodiments, a power connector (not shown) may reside on the base 22 and be configured to connect to an external power source.

The power source 133 may also be coupled, through at least one or more switches 137 and 138, to at least one temperature control element (not shown in FIG. 1) in the container 25 and/or reservoir 52 for heating and/or cooling the media so that the temperature within the container 25 remains within a desired range. Such switches 137 and 138 are coupled to and controlled by the controller 110. When the controller 110 places either of the switches 137 or 138 in an open state, no current flows through such switch 137 or 138 thereby disabling the temperature control element that is coupled to it. However, when either of the switches 137 or 138 is in a closed state, current flows through such switch 137 or 138 thereby enabling the temperature control element that is coupled to it.

To assist with the operation of the temperature control elements, at least one temperature sensor (not shown in FIG. 1), such as a thermistor or thermal coupler, may be used to detect a temperature of the media or the environmental conditions in the container 25. For example, at least one temperature sensor may be located within the container 25 and/or the reservoir 52. If a detected temperature is below a first threshold, the control logic 115 of the controller 110 may be configured to close one or more of the switches 137 and/or 138 to enable at least one of the temperature control elements. The enabled temperature control element heats the media and/or the environment within the container 25. If the detected temperature then exceeds a second threshold, which is higher than the first threshold, the control logic 115 then opens the previously closed switch 137 and/or 138 to disable the temperature control element. Accordingly, the temperature within the container 25 can be maintained within a desired range approximately between the first and second thresholds.

In one exemplary embodiment, a temperature sensor within the container 25 is used to control the switch 138, and a temperature sensor (not shown in FIG. 1) within the reservoir 52 is used to control the switch 137. However, other techniques for controlling the switches 137 and 138 are possible, and it is possible for the same temperature sensor to be used to control both switches 137 and 138. In fact, it is possible for a single switch 137 or 138 to be used to control the activation states of temperature control elements in both the container 25 and the reservoir 52 such that these temperature control elements are simultaneously enabled and disabled. In other embodiments, it is possible for a temperature control element to only exist in either the container 25 or the reservoir 52, and other locations for temperature control elements are possible as well.

Figure 7:
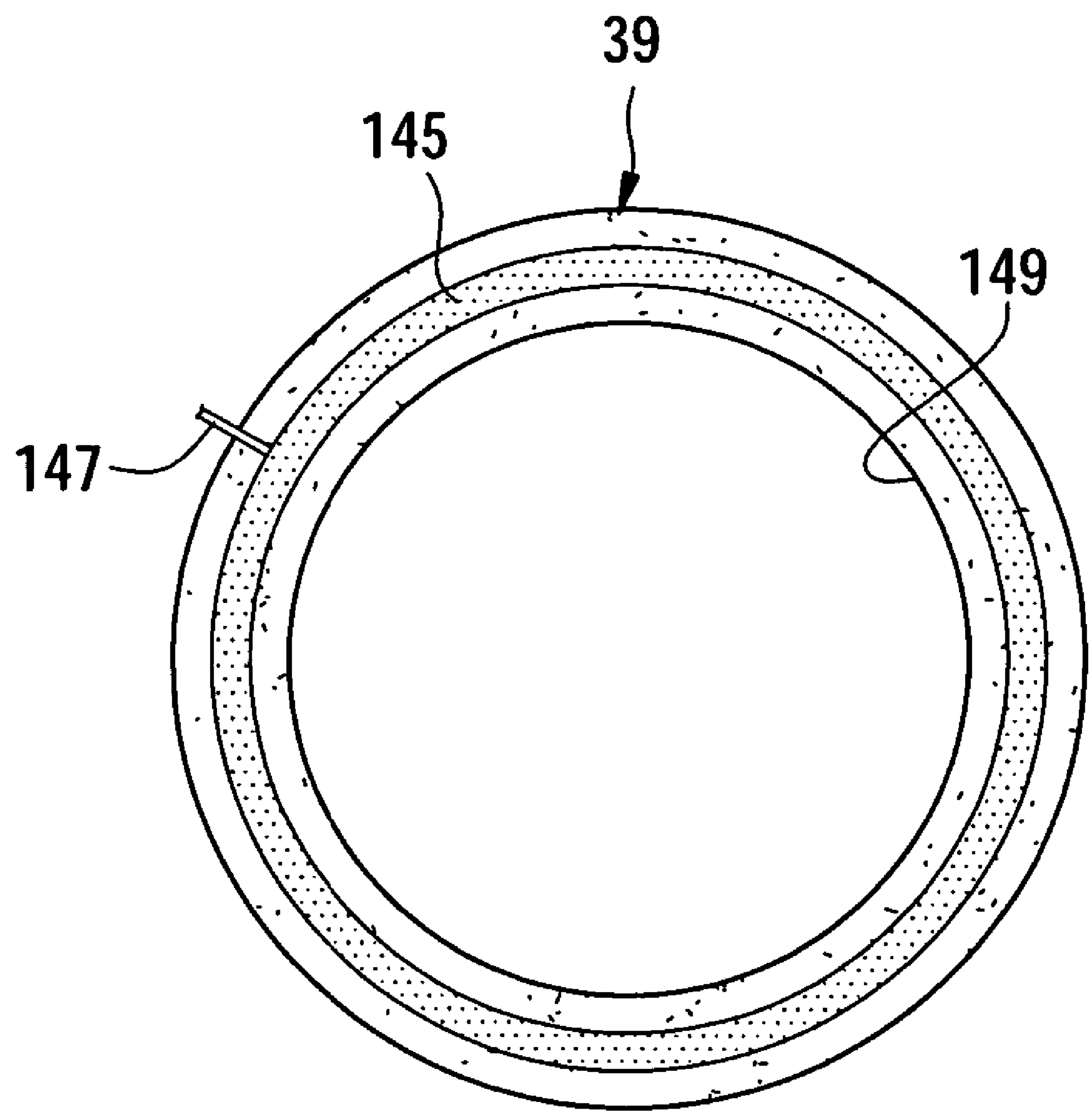
FIG. 7 is a top view of a lower gasket depicted in FIG. 2.

FIG. 7 depicts an exemplary temperature control element 145 residing on the lower gasket 39. The temperature control element 145 comprises a strip of resistive material that emits heat when electrical current is passed through it. The temperature control element 135 is coupled to an electrical connection 147 which extends to the switch 138 (FIG. 1). A hole 149 in the gasket 39 permits viewing of the culture within the container 25 through the transparent lower plate 33. Other locations for the temperature control element 145 are possible in other embodiments. Further, a temperature control element (not shown) may be mounted on the upper gasket 38 in a similar manner in addition to or in lieu of the temperature control element 145 shown by FIG. 7.

When the switch 138 is closed and electrical current is passed through the temperature control element 145, heat from the element 145 warms the gasket 39, which is preferably composed of a thermally conductive material. Heat is emitted from the gasket 39 into the environment within the container 25, as well as the media in the lower channel 43 (FIG. 2). FIG. 2 shows an exemplary temperature sensor 151, such as a thermistor, that is mounted on an inner wall of support member 37 and may be used to control operation of the temperature control element 145, as described above.

In other embodiments, it is possible for the temperature control element 145 to absorb heat from the media such that it can be used to cool the media. Thus, if a temperature sensed by a temperature sensor, such as sensor 151, rises above a specified threshold, then the controller 110 can be configured to enable the temperature control element 145 in an effort to lower the sensed temperature below the specified threshold or another threshold. Multiple temperature control elements may be used so that the media can be either heated or cooled based on sensed temperatures of the media. For example, if the media temperature rises above a first threshold, the controller 110 may activate one temperature control element to cool the media, and if the media temperature falls below a second threshold, which is lower than the first threshold, then the controller 110 may activate another temperature control element to heat the media. Thus, the temperature of the media can be controlled such that it remains within a temperature range between approximately the first and second thresholds.

Note that various other techniques may be used to control the activation states of any of the temperature control elements. For example, some conventional control elements detect a change in voltage across conductive components of the temperature control element in order to sense temperature. Such a temperature control element may be used thereby obviating the need of separate temperature sensors, such as sensor 151.

Figure 8:
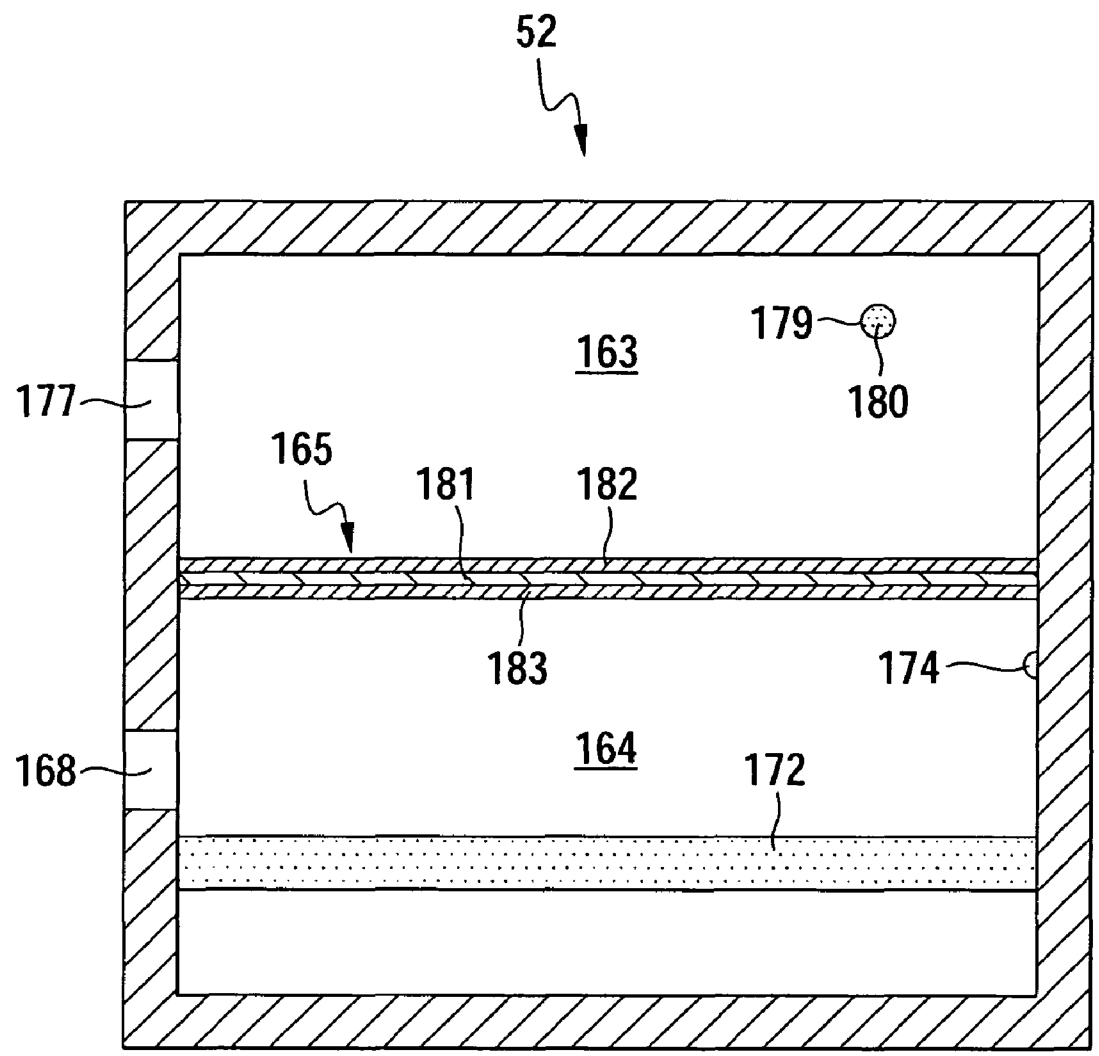
FIG. 8 is a cross-sectional view of a reservoir depicted in FIG. 1.

FIG. 8 depicts a cross-sectional view of the reservoir 52 depicted in FIG. 1. As shown by FIG. 8, the reservoir 52 has an upper chamber 163 that is separated from a lower chamber 164 by a gas permeable, hydrophobic membrane 165. Media is pumped into the chamber 164 by the pump 55 (FIG. 1) through an opening 168 in the wall of the reservoir 52. The media entering the chamber 164 displaces media already in the chamber 164 forcing media through hose 75 (FIG. 1) and into the container 25 via lower channel 43 (FIG. 2).

The chamber 164 is gas-tight except for the gas permeable membrane 165, the opening 168 through which media flows from hose 69 (FIG. 1) flows, and an opening (not shown) through which media flows to hose 75 (FIG. 1). Moreover, gas external to the reservoir 52, container 25, pump 55, and hoses 57 and 75 can access the media only through the gas permeable membrane 165. Further, the membrane 165 preferably filters the gas moving through it so that the gas entering the chamber 164 through membrane 165 is not significantly contaminated. In this regard, the membrane 165 acts as a barrier to contamination. Thus, the media in the apparatus 20 can only be contaminated by contaminants that are of a sufficiently small size to enable passage through the membrane 165.

As shown by FIG. 8, a temperature control element 172 may be mounted on an inner wall of the reservoir 52. The temperature control element 172 may be mounted on other walls of the reservoir 52, such as the inner wall that forms the bottom surface of the reservoir 52 facing the membrane 165. The temperature control element 172 is electrically coupled to the switch 137 (FIG. 1). When the switch 137 is closed and electrical current is passed through the temperature control element 172, heat from the element 172 warms the media in the chamber 164 thereby affecting the temperature of the environment in the container 25 when the warmed media is forced into the container 25.

Gas from the mixer 77 (FIG. 1) enters the upper chamber 163 through a hole 177 in a wall of the reservoir 52. A hole 179 within a wall of the reservoir 52 allows gas in the chamber 163 to vent to the atmosphere. A filter 180 within the hole 177 preferably filters any gas passing through the hole 180 in an effort to reduce the contaminants within the reservoir 52.

The membrane 165 is sufficiently permeable to gas to permit a desired rate of gas exchange between the gas within the chamber 163 and media within the chamber 164. In addition, the gas permeable membrane 165 forms a water tight seal between the chambers 163 and 164 so water cannot pass from one reservoir chamber to the other. Indeed, water can move through the container 25, the hoses 57 and 69, the pump 55 and the chamber 164 of the reservoir 52 but is prevented from escaping from any of these components to the atmosphere. Further, water is also prevented from entering any of these components from the atmosphere. Thus, the humidity within the container 25 remains substantially constant.

The membrane 165 can be composed of various types of material. In one exemplary embodiment, the material of the membrane 165 is a hydrophobic medical membrane product (product number MMT-323) sold by W.L. Gore & Associates, Inc. This material has 100% expanded polytetrafluoroethylene (PTFE) layer with at least one nonwoven polyester support layer to enhance the mechanical integrity of the PTFE layer, which is brittle. Moreover, in one embodiment, the membrane 165 is a multi-layer component, with a PTFE layer 181 sandwiched between two support layers 182 and 183 of nonwoven polyester. To provide sterility, the pore size of the PTFE is preferably less than 0.22 microns. The support layers 182 and 183 are permeable and may have pore sizes much greater than 0.22 microns, since the PTFE ensures sterility of the gas exchange. Thus, the outer support layer 182 exposed to gas within the chamber 163 acts as a pre-filter with the PTFE layer 181 providing more fine filtering. In this regard, gas that passes through the membrane 165 from the chamber 163 is first filtered by the outer support layer 182, which has a larger pore size than the PTFE, and the gas is then filtered by the PTFE layer 181. In an embodiment that uses the aforedescribed medical membrane sold by W.L. Gore & Associates, Inc., the pore size of the PTFE layer 181 is about 0.2 microns, and the membrane 165 allows passage of approximately 100 $cm^3$ air through 1.0 $in^2$ orifice at 4.88" $H_20$ pressure drop within 9 to 24 seconds. The airflow allowed by this membrane is approximately 3.2 LPM/$cm^2$ to 8.5 LPM/$cm^2$ at 1 bar (15 pounds per square inch). Further, the thickness of the membrane 165 is between approximately 0.2 mm and 0.41 mm. However, the membrane 165 may be composed of other types of gas permeable material in other embodiments.

Figure 9:
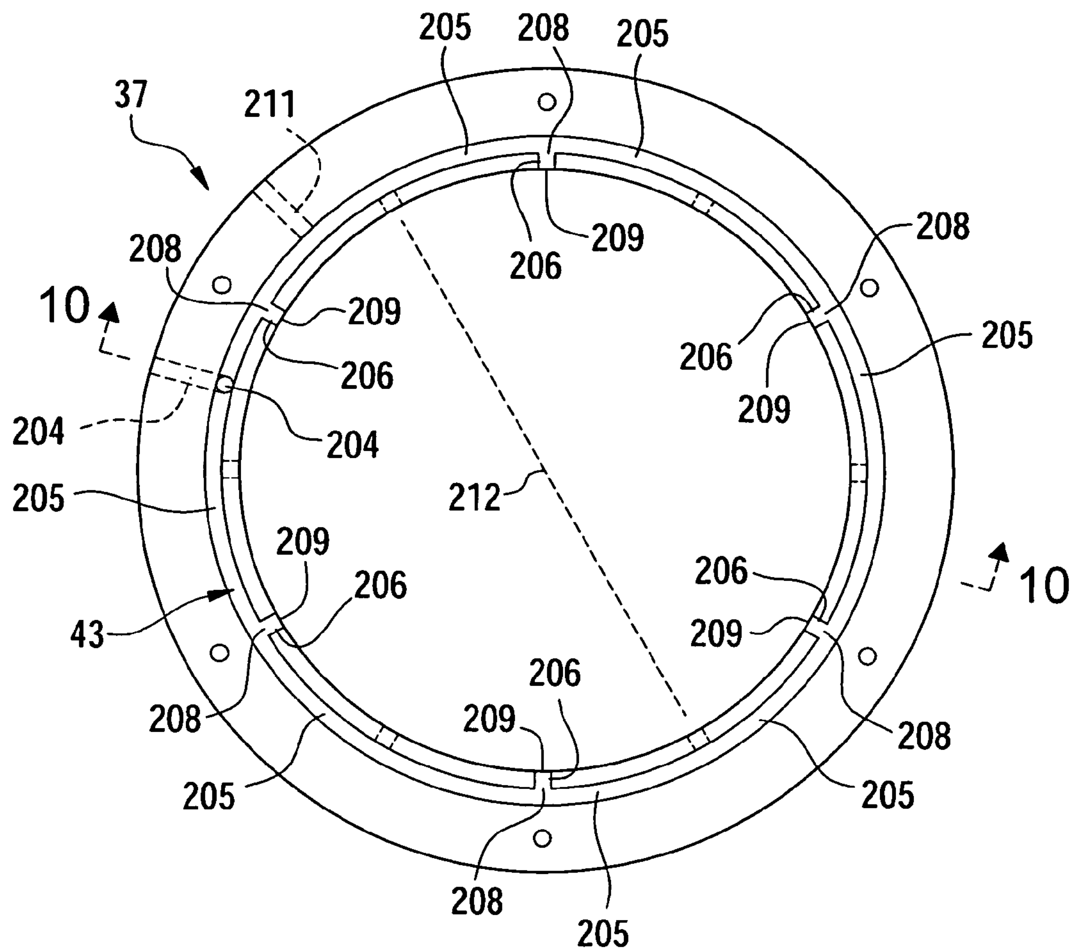
FIG. 9 is a bottom view of a support member depicted in FIG. 2.
Figure 10:
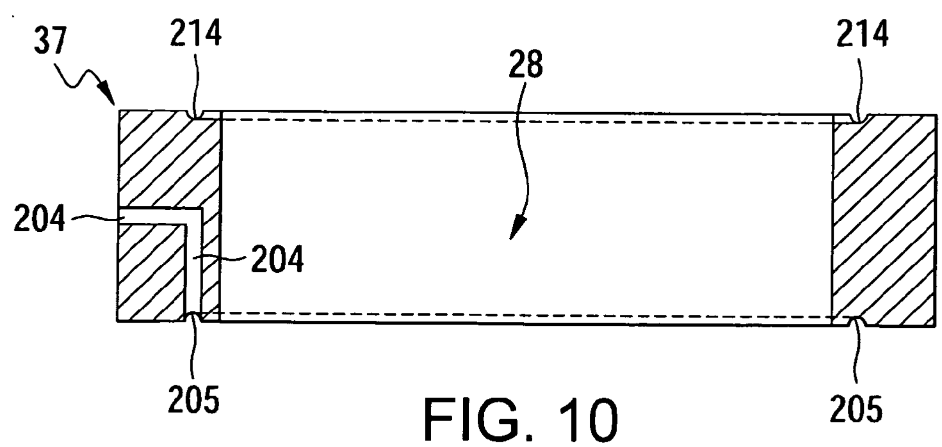
FIG. 10 is a cross-sectional view of the support member depicted in FIG. 9.

Note that various configurations of the channels 42 and 43 within the container 25 of FIG. 2 are possible. FIG. 9 depicts a bottom view of the exemplary support member 37 shown in FIG. 2. In the exemplary embodiment depicted by FIG. 9, a first portion of the channel 43, referred to herein as the "input leg 204" receives media from the hose 75 (FIG. 1) that is coupled to reservoir 52. Referring to FIGS. 9 and 10, the input leg 204 has a bend of approximately 90 degrees and extends from the hose 75 to another portion of the channel 43, referred to herein as the "transport leg 205." The transport leg 205 is circular and transports the media from the input leg 204 around a periphery of the chamber 28, although other shapes of the transport leg 205 are possible in other embodiments. Portions of the channel 43, referred to herein as "inlet legs 206," extend from the transport leg 205 to the chamber 28. Moreover, media passes through the input leg 204 to the transport leg 205, and the media travels around a perimeter of the chamber 28 via the transport leg 205. As the media is traveling through the transport leg 205, portions of the media pass from the transport leg 205 through the various inlet legs 206 and into the chamber 28. In this regard, one end of each respective inlet leg 206 has a mouth 208 that allows passage of media from the transport leg 205 to the inlet leg 206, and the other end of each respective inlet leg 206 has a mouth 209 that allows passage of media from the inlet leg 206 to the chamber 28.

The number and positioning of the mouths 209 of the inlet legs 206 used to deliver media to the chamber 28 affect the amount of shearing turbulence within the chamber 28. For example, if media is delivered to the chamber 28 via only a single mouth 28, then it is likely that media shearing turbulence will damage the culture in the chamber 28. Having multiple mouths 209 to deliver the media to the chamber 28 helps to reduce the shearing turbulence and to prevent damage to the culture. Further, having mouths 209 aligned with one another on opposite sides of the inner wall of the support member 37 helps to reduce shearing turbulence as well. For example, in FIG. 9, each mouth 209 is substantially aligned with another corresponding mouth 209 through a diameter of the support member 37, which is in the shape of a ring in the instant embodiment.

For instance, dotted line 212, which extends through the center of the support member 37, shows that the two corresponding mouths 209 from which it extends are aligned in that media exiting either of these mouths 209 would be directed toward the other mouth 209. Thus, as media exits from each of these two corresponding mouths 209, the momentum of the media from each of these mouths 209 effectively counteracts the momentum of the media from the other corresponding mouth 209. In this regard, when corresponding mouths 209 are precisely aligned, as illustrated in FIG. 9, the media from each of the two corresponding mouths 209 generally travel along the same line or path but in opposite directions meeting close to the center of the chamber 28. Such an effect helps to bring the media to rest sooner and with less adverse effect to the culture within the chamber 28, as compared to an embodiment in which the mouths 209 are not aligned. In general, the closer that the two corresponding mouths 209 are aligned, the better the adverse effects of shearing turbulence are suppressed for the media that egresses from these two corresponding mouths 209.

Each mouth 209 within the container 25 similarly corresponds with one of the other mouths 209 such that the momentum of the media exiting each mouth 209 is counteracted by the media from its corresponding mouth 209. FIG. 9 shows six inlet legs 206 and mouths 209, but any number of inlet legs 206 and mouths 209 are possible in other embodiments.

Figure 11:
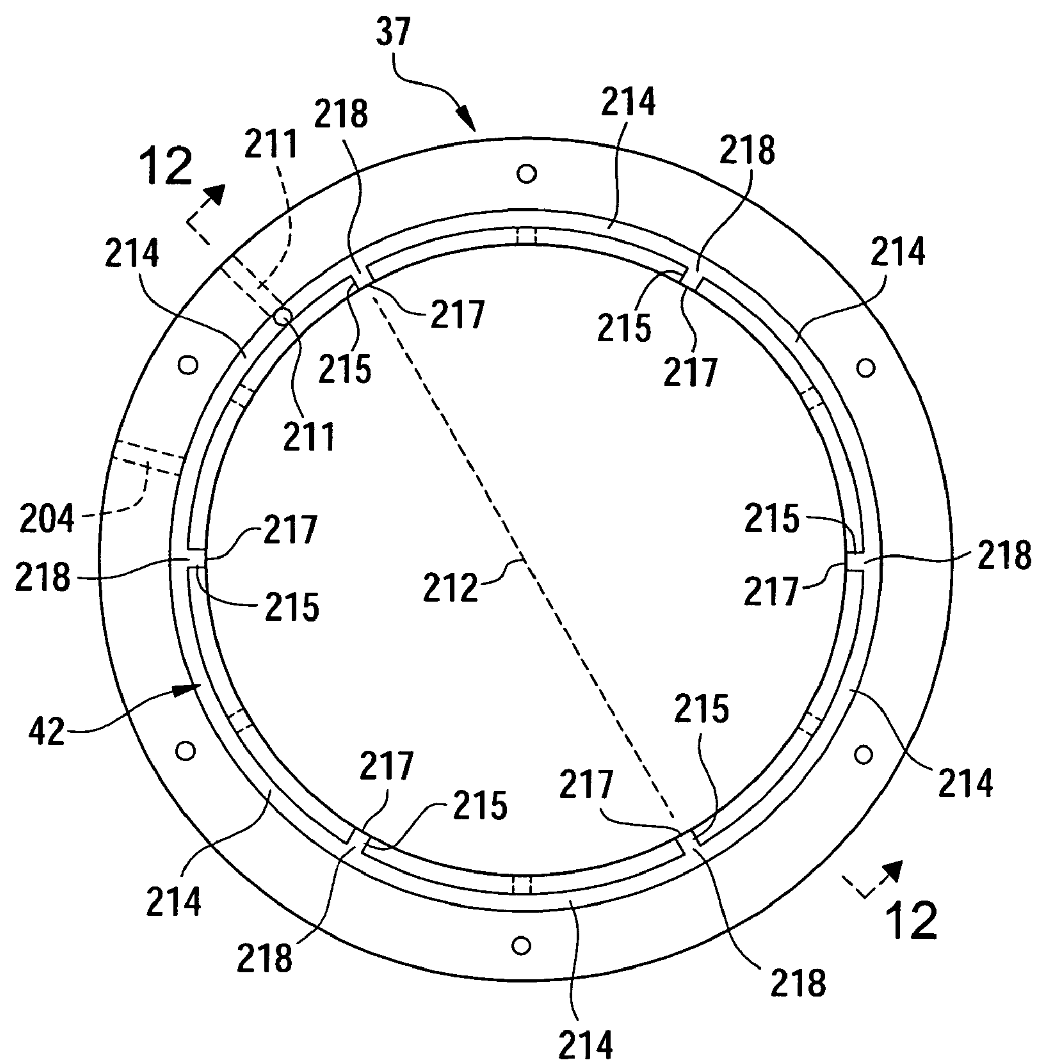
FIG. 11 is a top view of the support member depicted in FIG. 2.
Figure 12:
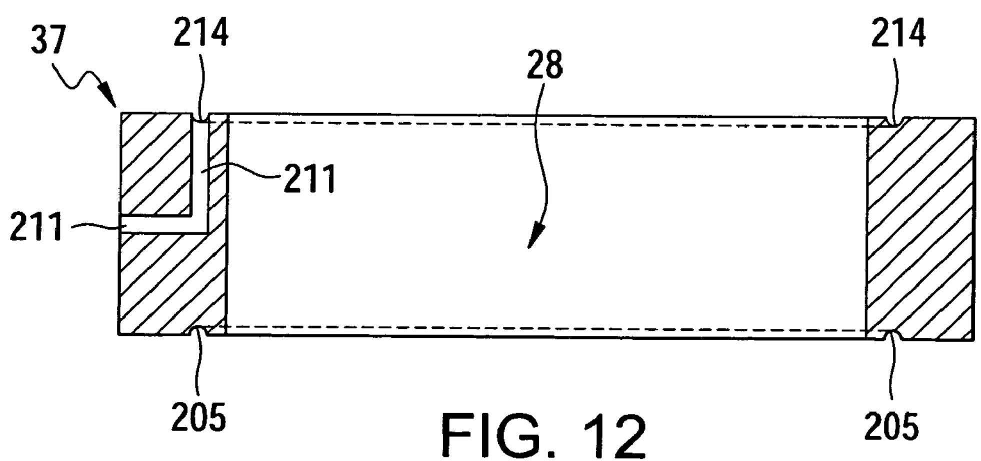
FIG. 12 is a cross-sectional view of the support member depicted in FIG. 11.

FIG. 11 depicts a bottom view of the exemplary support member 37 shown in FIG. 2. Media is drawn out of the container 25 through a portion of the channel 42, referred to herein as the "output leg 211." Referring to FIGS. 11 and 12, the output leg 211 has a bend of approximately 90 degrees and extends from the hose 57 (FIG. 1) to another portion of the channel 42, referred to herein as the "transport leg 214." The transport leg 214 is circular and transports the media around a periphery of the chamber 28 to the output leg 211, although other shapes of the transport leg 214 are possible in other embodiments. Portions of the channel 42, referred to herein as "outlet legs 215" extend from the transport leg 214 to the chamber 28. Moreover, media passes through the outlet legs 215 to the transport leg 214, and the media travels around a perimeter of the chamber 28 via the transport leg 214. When media reaches the mouth of the output leg 211, the media passes into the output leg 211 and out of the container 25.

One end of each respective outlet leg 215 has a mouth 217 that allows passage of media from the chamber 28 to the inlet leg 215, and the other end of each respective inlet leg 215 has a mouth 218 that allows passage of media from the inlet leg 206 to transport leg 214. Note that the mouths 217 of the outlet legs 215 are preferably offset with respect to the mouths 209 of the inlet legs 206, as shown by FIGS. 9 and 11. Indeed, in the embodiment shown by FIGS. 9 and 11, each mouth 217 is located about half-way between two respective mouths 209 in a radial direction about the center of the chamber 28 and vice versa. Offsetting of the mouths 209 and 206 such that they are not directly above or below one another may help to reduce shearing and/or turbulence within the chamber 28 and may help reduce the likelihood that the media entering the chamber 28 via mouths 206 will be immediately drawn out of the chamber 28 via mouths 217.

In one exemplary embodiment, the length of the base 22 is less than about 10 inches, and the width of the base is about 4 inches, although other dimensions are possible in other embodiments. Indeed, in the instant embodiment, the apparatus 20 is sufficiently small and lightweight so that it can be carried by a user. For example, the apparatus 20 may be carried to a microscope 36 (FIG. 4) so that a user can view the culture within the container 25 through the upper plate 32. During such viewing, a light source 34 can be used to emit light through the lower plate 33 to enable better viewing of the culture. Moreover, such transporting and viewing can be accomplished while the conditions within the container 25 are being monitored and controlled by the controller 110 so that the "blood gases," temperature, humidity, acidity, and possibly other environmental conditions within the container 25 are maintained within a desired range. Such transporting and viewing can also be accomplished without exposing the culture to significant contamination since all external gas can come into contact with the media only by passing through the membrane 165 (FIG. 8), which is a barrier to contamination.

Figure 13A:
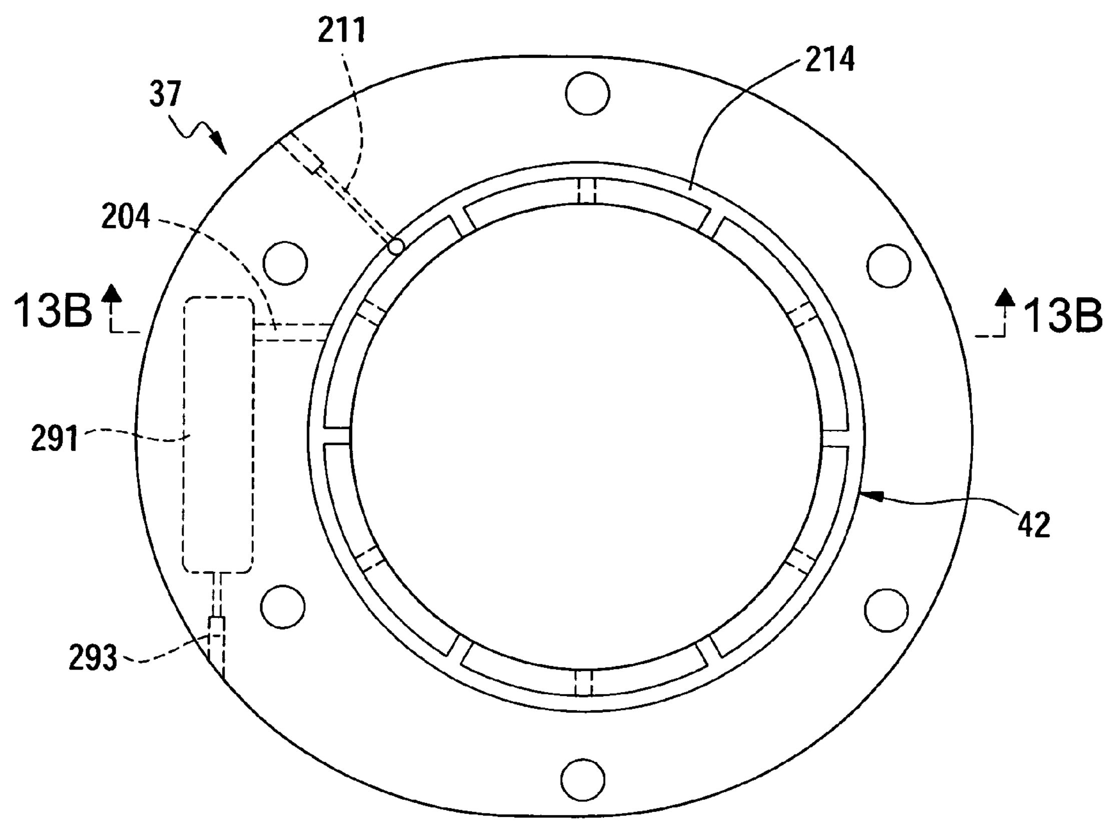
FIG. 13A is a top view of the support member when the reservoir is integrated with the cell culture container.

Various modifications can be made to the apparatus 20 without departing from the principles of the present disclosure. For example, the container 25 and the reservoir 52 can be integrated into a single, unitary structure. In such an embodiment, a compartment of the container 25 can be used to form two chambers separated by a gas permeable membrane, and another compartment can be used for growing cells. In such an embodiment, a channel preferably extends between the compartments so that media can flow from the reservoir compartment to the other compartment. FIG. 13A depicts a top view of an exemplary incubation apparatus 20 having such a container 25.

Figure 13B:
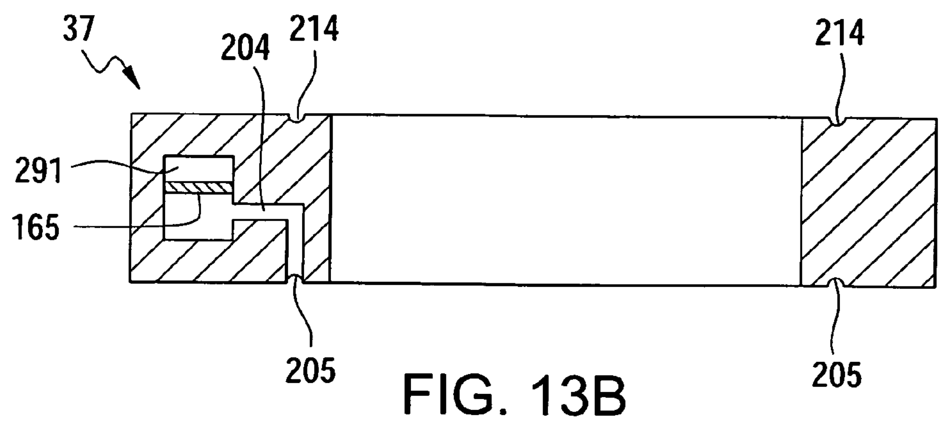
FIG. 13B is a cross-sectional view of the support member depicted in FIG. 13A.

In this regard, a compartment 291 serves as reservoir for holding media that is pumped into the chamber 28. The inlet leg 204 extends from the compartment 291 to the transport leg 205. Further, a channel 293 extends from the compartment 291 to the hose 87 (FIG. 1) to allow gas to enter the compartment 291. Another channel (not shown) below channel 293 extends from the compartment 291 to the hose 69 (FIG. 1) to allow media to be pumped into the compartment 291. As shown by FIG. 13B, the compartment 291 is preferably divided by a gas permeable membrane 165 (FIG. 8) similar to the reservoir 52 of FIG. 8 that allows gas exchange to occur without contaminating the media. The gas from channel 293 enters the compartment 291 in an upper chamber of the compartment 291 above the membrane 165, and media from channel 293 enters the compartment 291 in a lower chamber of the compartment 291 below the membrane 165 such that gas must pass through the membrane 165 to diffuse with the media.

Figure 14:
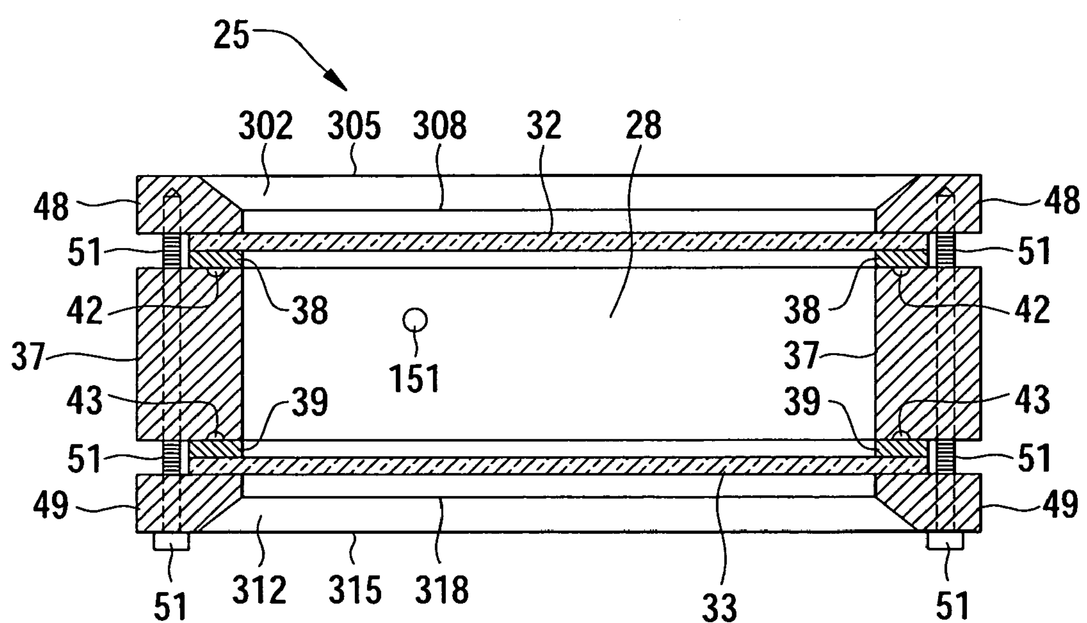
FIG. 14 is a cross-sectional view of an exemplary cell container, such as is depicted in FIG. 1.

FIG. 14 depicts an exemplary embodiment of the container 25. The embodiment shown by FIG. 14 is similar to the embodiment shown by FIG. 2. However, the upper support member 48 has an inclined surface 302. In this regard, the surface 302 slopes downward from an upper edge 305 to a lower edge 308. Further, the lower support member 49 also has an inclined surface 312. In this regard, the surface 312 slopes upward for a lower edge 315 to an upper edge 318.

Figure 15:
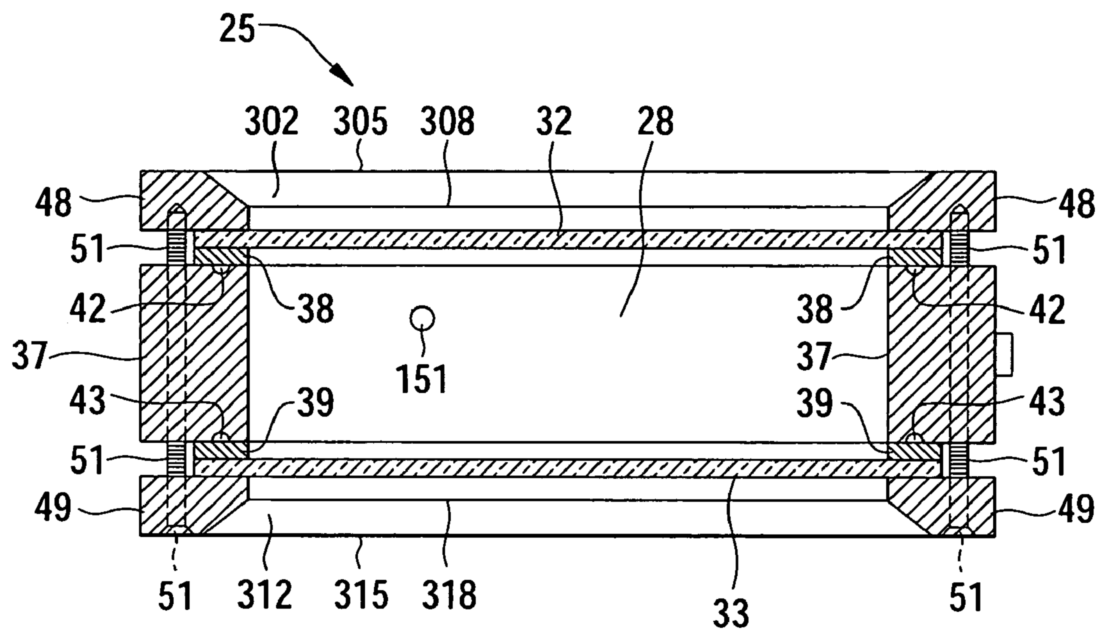
FIG. 15 is a cross-sectional view of an exemplary cell container, such as is depicted in FIG. 1.

FIG. 15 depicts another exemplary embodiment of the container 25. The embodiment shown by FIG. 15 is similar to the embodiment shown by FIG. 14. However, the screws 51 passing though each of the support members 37, 48, and 49 are countersunk in the lower support member 49 such that the heads of the screws 51 are not visible in FIG. 15.

Figure 16:
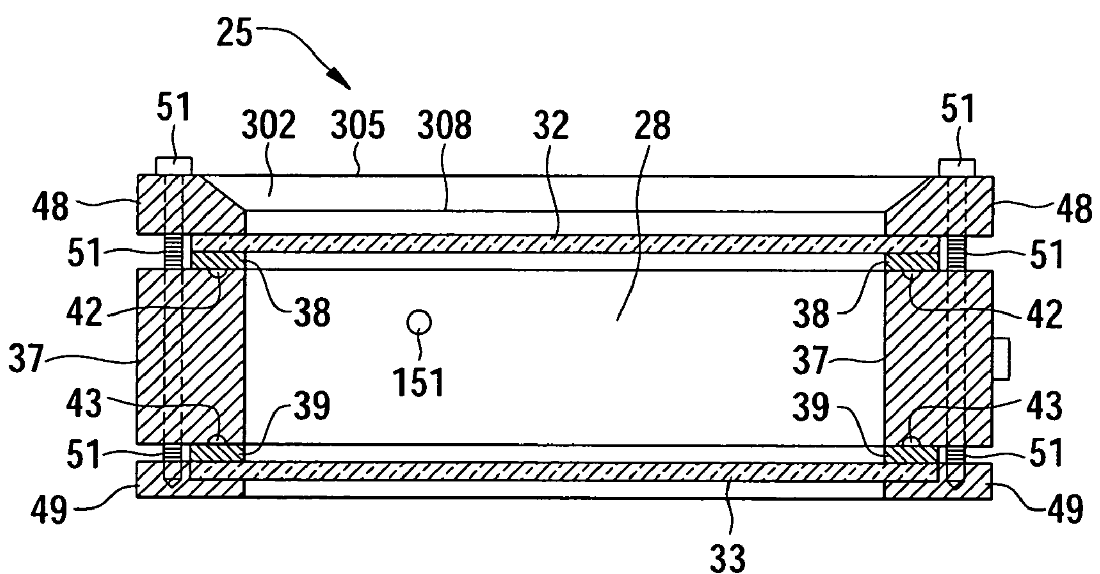
FIG. 16 is a cross-sectional view of an exemplary cell container, such as is depicted in FIG. 1.

FIG. 16 depicts yet another exemplary embodiment of the container 25. The embodiment shown by FIG. 16 is similar to the embodiment shown by FIG. 14. However, to give the container 25 a lower profile, the thickness of the lower support member 49 is reduced compared to that of FIG. 14. Further, the screws 51 are screwed into the container 25 in an opposite direction, as compared to the embodiment of FIG. 14, such that the heads of the screws 51 contact an upper surface of the upper support member 48 instead of the lower surface of the lower support member 49. Various other configurations of the container 25 are possible in other embodiments.

Note that, in an exemplary embodiment, the container 25, the pump 55, and the reservoir 52 are detachably coupled to the base 22 so that each component that contacts media can be removed from the apparatus 20 upon completion of an experiment. The components that do not contact media may be either detachably coupled to or permanently mounted on the base 22. Moreover, integrating the reservoir 52 and the container 25 into a single unitary structure, as previously described above, may facilitate removal of these components from the base 22. Note that various techniques may be used to detachably couple the container 25, the pump 55, and the reservoir 52. For example, these components can be screwed or clipped onto the base 22 by screws or clips, respectively. Alternatively, these components can be friction fitted to the base 22.

Moreover, after an experiment, the reservoir 52 can be disconnected from hose 87, and the containers, reservoir 52, and pump 55, as well as hoses 57 and 69, can be removed. The removed components can be replaced with new components, or these components can be sterilized and re-used. In this regard, sterilization of the components may be facilitated by removing the components and taking them to a more ideal location for sterilization. Further, if some of the non-removed components on the base 22 are incompatible with the sterilization techniques, then removing the container 25, the hoses 57 and 69, the pump 55, and the reservoir 52 allows these components to be sterilized without damaging the non-removed components. Sterilizing the removed components or replacing these components with new components reduces the likelihood that a previously performed experiment will contaminate the next experiment.

Figure 17:
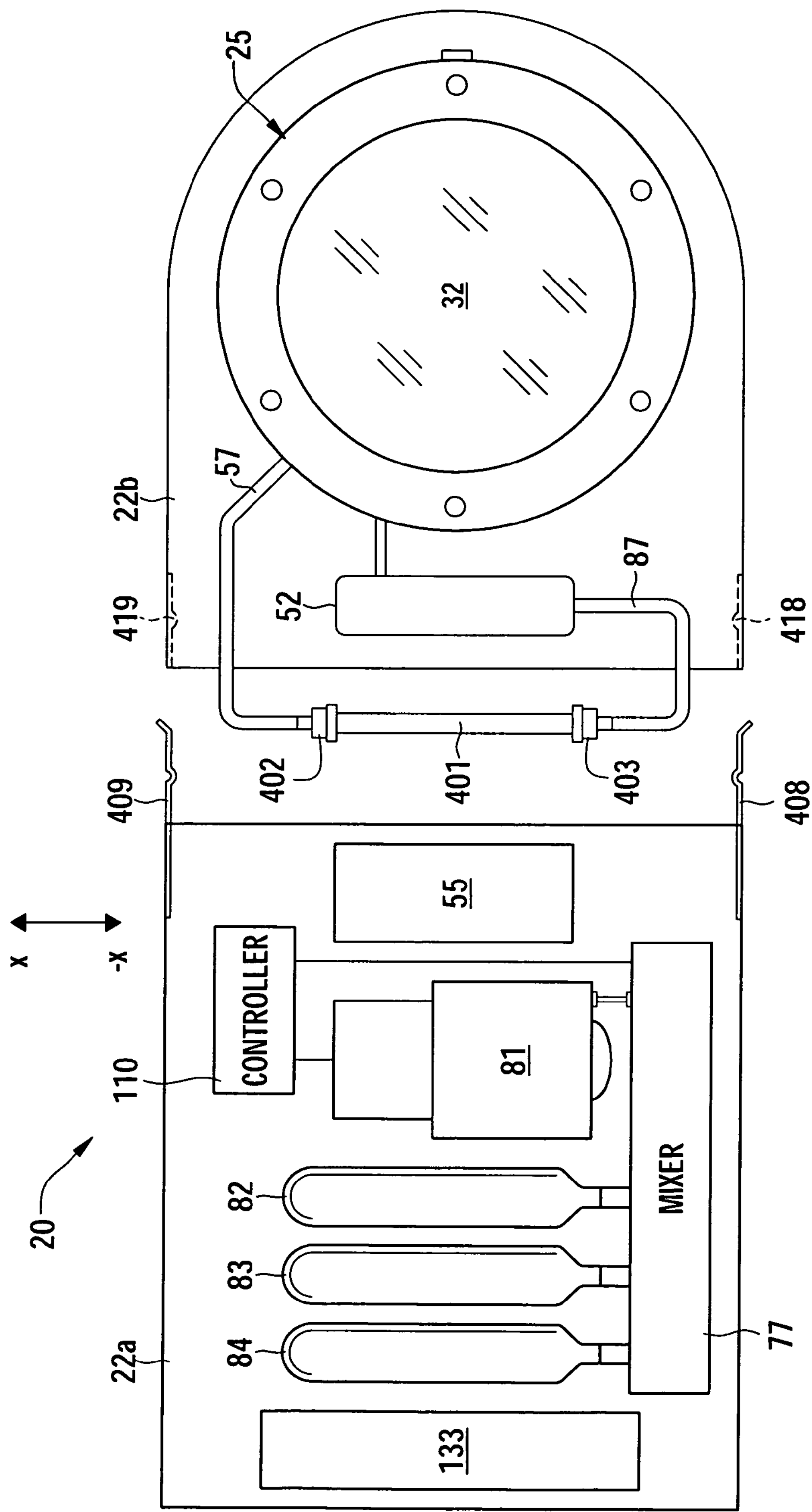
FIG. 17 illustrates a top view of a self-contained incubation apparatus having a segmented base in accordance with an exemplary embodiment of the present disclosure.

FIG. 17 depicts an exemplary embodiment in which the base 22 is segmented into two segments 22*a* and 22*b*. The reservoir 52 and container 25 reside on segment 22*b*, and other components of the apparatus 20 reside on segment 22*a*, as shown by FIG. 17. The reservoir 52 and container 25 can be detachably coupled to segment 22*a* by virtue of the segment 22*b* being detachably coupled to the segment 22*a*, as will be described in more detail hereafter.

In this regard, a hose segment 401 having a hose interface 402 and 403 at each end of the segment 401 couples hose 57 to hose 87. In particular, media drawn out of the container 25 through hose 57 flows through segment 401 to hose 87 during operation. During operation, the segment 55 fits into or is coupled to the remaining structure of pump 55. However, the segment 401 is removable from the pump 55, as shown by FIG. 17. Clips 408 and 409 slide into channels 418 and 419, respectively, to connect segments 22*a* and 22*b*. The clips 408 and 409 may be spring loaded to push the clips in the x or −x direction so that frictional forces help to keep the segments 22*a* and 22*b* connected when the clips are inserted into the channels 418 and 419. However, these forces can be overcome by pulling the segments 22*a* and 22*b* apart so that the portions 22*a* and 22*b* can be disconnected, as shown by FIG. 17.

Thus, after an experiment has been performed, the segment 401 may be removed from the remaining structure of the pump 55, and the segment 22*b* may be disconnected from the segment 22*a* by pulling these segments apart until the clips 408 and 409 slide out of the channels 418 and 419. The segment 22*b* and the components mounted thereon may then be cleaned without exposing the segment 22*a* or the components mounted thereon to the cleaning process. In another exemplary embodiment, it is possible for the entire structure of the pump 55 to reside on the segment 22*b*. It is also possible for other components shown as residing on segment 22*a* in FIG. 17 to reside on segment 22*b* instead.

Various methodologies for controlling the environmental conditions within the container 52 are possible. For example, throughout the course of an experiment, the control logic 115 may be configured to control the activation state of the temperature control element 145 (FIG. 7) in the container 25 based on a first threshold, referred to as an “upper threshold,” and a second threshold, referred to as the “lower threshold,” according to techniques described above. In such an example, the temperature within the container 25 continuously remains within the same desired temperature range approximately between the upper and lower thresholds. However, for another experiment, it may be desirable to dynamically update the thresholds used to control the activation state of the temperature control element 145 such that the temperature range within the container 25 fluctuates.

As an example, it is common for the body temperature of many mammals to change over the course of a day. In particular, the body temperature of a particular mammal may be relatively high during daytime hours when the mammal is more active and decrease at night when the mammal becomes less active (e.g., sleeps). For a tissue culture of such a mammal, better experiment results may be obtained by lowering the temperature within the container 25 during some periods (e.g., at night) and increasing the temperature within the container 25 during other periods (e.g., during daytime hours). To enable the control logic 115 to control the conditions within the container 28 based on time, the control logic 115 may receive inputs from the clock 131 (FIG. 6).

Various techniques may be employed to achieve the foregoing. In one exemplary embodiment, the control logic 115 is configured to update the thresholds used to control the temperature control elements 145 (FIG. 6) and/or 172 (FIG. 7). For example, at 6:00 a.m. each day, the control logic 115 may be configured set the upper threshold for the temperature control element 145 to a first threshold, $T_{U1}$, and the lower threshold for the temperature control element 145 to another threshold, $T_{L1}$, which is slightly lower than $T_{U1}$. Thus, after 6:00 a.m. each day, if the temperature sensed via sensor 151 (FIG. 2) falls below $T_{L1}$, the control logic 115 activates the temperature control element 145 until the temperature reaches or exceeds $T_{U1}$. However, at 6:00 p.m. each day, the control logic 115 sets the upper threshold for the temperature control element 145 to a threshold, $T_{U2}$, which is lower than $T_{U1}$. At this time, the control logic 115 also sets the lower threshold for the temperature control element 145 to a threshold, $T_{L2}$, which is lower than $T_{L1}$. Thus, after 6:00 p.m. each day, if the temperature sensed via sensor 151 falls below $T_{L2}$, the control logic 115 activates the temperature control element 145 until the temperature reaches or exceeds $T_{U2}$. Note that the thresholds for the temperature control element 172, if employed, may be similarly controlled in such an example.

Accordingly, between the hours of 6:00 a.m. and 6:00 p.m., the temperature within the container 25 is kept within a first temperature range approximately between $T_{L1}$ and $T_{U1}$. However, between the hours of 6:00 p.m. and 6:00 a.m., the temperature within the container 25 is kept within a second temperature range approximately between $T_{L2}$ and $T_{U2}$. Such fluctuations in the temperature range may better simulate the actual body temperature of the mammal from which the tissue culture was taken, as compared to an embodiment in which the temperature range is substantially constant. Note that the aforedescribed algorithm for fluctuating the temperature range within the container 25 is presented for illustrative purposes, and it should be apparent that other algorithms are possible in other examples.

Further, the control logic 115 can be configured to change other conditions within the container 25 over time. For example, the control logic 115 may be configured to introduce a particular gas to the chamber 28 (FIG. 2) of the container 25 at a desired time so that the effect of this gas to the growth of the cells within the chamber 28 may be studied. For example, assume that the control logic 115 is configured to maintain a certain gas mixture, such as 95% air and 5% carbon dioxide, within the container 25. In such an example, the control logic 115 may control the states of valves 101 and 102 (FIG. 5), assuming that the container 82 (FIG. 1) coupled to the valve 102 is filled with carbon dioxide, such that the mixer 77 continuously delivers the desired $CO_2$/air mixture to the reservoir 52. In such an example, the valves 103 and 104 generally remain closed such that the gases in containers 83 and 84 do not affect the mixture delivered by the mixer 77.

However, at a desired time, the control logic 115 may temporarily open the valve 103 such that gas from the container 83 flows through the valve 103 and into the reservoir 52 to diffuse with the media in the chamber 164 (FIG. 8). The media diffused with this gas is eventually pumped into the chamber 28 (FIG. 2) of container 25, and the effect of this gas to the culture within the chamber 28 can then be observed. The gas from the container 83 may be introduced to the chamber 28 a single time during an experiment or at multiple times as may be desired.

Before an experiment is initiated, the control logic 115 may be programmed or otherwise configured to automatically control operation of the apparatus 20 even if the conditions within the container 25 are to be fluctuated over time, such as, for example, changing the temperature range maintained within the chamber 28 or the gases introduced to the chamber 28, as described above. However, if desired, the conditions within the container 25 may also be controlled via user inputs during an experiment.

As a mere example, a user may provide an input for increasing or decreasing the temperature range maintained within the container 25. The input may be submitted via user equipment, such as a computer (not shown), that is in communication with the communication interface 129 (FIG. 6), or the input may be submitted via user interface 132. Based on this input, the control logic 115 may be configured to adjust the thresholds used to control the activation states of the temperature control elements 145 and/or 172 so that the temperature within the container 25 is maintained as requested. Such an input may cause a permanent change such that the control logic 115 continues to control the temperature within the container 25 as requested by the user input until a new user input for controlling the temperature is received. In other examples, the may input only temporarily alter the conditions within the container. In this regard, after a specified amount of time has elapsed, the control logic 115 may revert to controlling the temperature within the container 25 based on a predefined algorithm.

Similarly, a user may provide an input for introducing a gas within a particular container 82-84 to the chamber 28 of the container 25. Based on this input, the control logic 115 may be configured to open at least one of the valves 82-84 such that the gas within the particular container 82-84 identified by the input is introduced to the chamber 28. Such an input may cause a permanent change such that the mixture delivered by the mixer 77 contains a certain percentage of the gas from the particular container 82-84 until a new user input for controlling the gas from the particular container 82-84 is received. In other examples, the input may only temporarily affect the distribution of gas from the particular container 82-84.

An exemplary use and operation of the apparatus 20 will now be described with particular reference to FIG. 1. For illustrative purposes, assume that, for the cells to be grown within the container 25, the ideal environmental conditions are 100% humidity within a mixture of 5% carbon dioxide and 95% air at 37 degrees Celsius. Initially, the cells are positioned in the container 25. In this regard, the container 25 may have a syringe port 252 (FIG. 1) that can be penetrated by a needle of a syringe to position a tip of the needle within the container 25. Then, the cells can be injected through a hole in the tip of the needle and into the container 25. The needle can then be withdrawn. Any known or future-developed syringe port may be used to implement the syringe port 252 shown in FIG. 1.

Similarly, media may be inserted into the container 25 via a syringe that also penetrates the syringe port 252. In the instant example, a sufficient amount of media is inserted to fill the container 25 as well as the media chamber 164 (FIG. 8) of reservoir 52. In this regard, as the chamber 28 of the container 25 is filled with media, the media not only fills the chamber 28 but some media is forced through channels 42 and/or 43 to the reservoir chamber 164.

Once the cells and media have been inserted into the chamber 28 of container 25, a user activates the components of the apparatus 20 by manually closing the switch 135 (FIG. 1). Thus, power is supplied to the controller 110, pumps 55 and 81, and mixer 77. If any of the components use a voltage different than the output voltage of the power source 133, such components may include circuitry (not shown) to reduce or otherwise regulate the voltage of the power signal provided to such components.

The control logic 115 selectively controls the valves 101-104 (FIG. 5) such that the mixer 77 transmits a desired gas mixture to the reservoir 52. In the instant example, the valves 101-104 are controlled such that carbon dioxide from one of the containers 82-84 is mixed with air from pump 81. In particular, the gas mixture provided by the mixer 77 is preferably composed of 5% carbon dioxide and 95% air.

Also, the pump 55 continuously pumps media from the container 25 and into the chamber 164 (FIG. 8) of the reservoir 52, although non-continuous operation of the pump 55 is also possible in other examples. Thus, media within the chamber 28 (FIG. 2) is pumped through the upper channel 42 and hose 57 to pump 55, which then forces the media to the reservoir 52 through hose 69. The gas mixture within the reservoir chamber 163 (FIG. 8) passes through the gas permeable membrane 165 within the reservoir 52 and diffuses with the media in the chamber 164. The media pumped into the chamber 164 displaces media already in the chamber 164 causing it to be forced out of the chamber 164 through hose 75 (FIG. 1). This media passes through the lower channel 43 (FIG. 2) and into the chamber 28 of the container 25. As described above, the media passing through channel 43 egresses out of the channel 43 and into the chamber 28 through a plurality of mouths 209 so that the momentum of each stream of media entering the chamber 28 is counteracted, at least partially, by at least one other stream of media entering the chamber 28 through at least one other mouth 209. Thus, the adverse effects of media shearing and/or turbulence within the chamber 28 are reduced.

If the temperature measured by the temperature sensor 151 (FIG. 2) within the chamber 28 falls below a specified threshold, such as 37 degrees Celsius in the instant example, then the control logic 115 activates the temperature control element 145 (FIG. 7) such that it emits heat. The heat from the element 145 warms the contents of the chamber 28. The control logic 115 keeps the temperature control element 145 activated until the temperature sensed by the temperature sensor 151 reaches the specified threshold or another threshold slightly higher than this threshold.

If the temperature measured by the temperature sensor 174 (FIG. 8) within the reservoir 52 falls below a specified threshold, such as 37 degrees Celsius in the instant example, then the control logic 115 activates the temperature control element 172 such that it emits heat. The heat from the element 145 warms the contents of the chamber 164. The control logic 115 keeps the temperature control element 172 activated until the temperature sensed by the temperature sensor 174 reaches the specified threshold or another threshold slightly higher than this threshold. Keeping the media in the chamber 164 at a temperature close to the desired temperature of the container 25 helps to keep the contents of the container 25 at or close to the desired temperature.

Moreover, by controlling the temperature control elements 145 and/or 172, as described above, the temperature of the environment within the container 25 is maintained at a desired temperature. Further, the humidity and acidity within the container 25 remain substantially constant. Accordingly, conditions conducive to cell growth are maintained within the container 25. Further, since the apparatus 20 is of sufficiently small scale to be portable, the apparatus 20 can be carried to or placed in a variety of locations without significantly impacting cell growth. Indeed, it is unnecessary to store the apparatus 20 in a conventional incubator. Not only is convenience enhanced, but the need for purchasing an expensive and bulky conventional incubator may be eliminated. Additionally, the cells within the container 25 can be observed, for long periods of time, via the transparent upper and lower plates 32 and/or 33 (FIG. 2) without removing the cells from a controlled environment and without exposing the cells to contamination.

Note that it is unnecessary for all of the components of the apparatus to reside on or be formed on a single base 22. For example, in one exemplary embodiment, the container 25, media pump 55, reservoir 52, controller 110 and switches 137 and 138 reside on a single base 22. However, the mixer 77, air pump 81, containers 82-84, and power source 133 reside elsewhere, such as on a separate base (not shown). However, the power source 133 is electrically coupled to the other components as shown in FIG. 1, and the mixer 77 is coupled to the reservoir 52. Various other configurations are also possible. Indeed, any of the components of the apparatus 20 may be reside at a location other than the base 22.

Note that, in the embodiments described above, each of the plates 32 and 33 is described as transparent. However, to enable viewing of the culture without opening container 25, it is sufficient if only one of the plates 32 or 33 is transparent. The other plate is preferably light permitting to enable better illumination of the culture. However, it is possible for either of the plates 32 or 33 to be opaque. It is also possible for one or more light sources (not shown) such as light emitting diodes to be positioned in the chamber 28. Such light sources may be particularly advantageous if either of the plates 32 or 33 is opaque.

Now, therefore, the following is claimed:

1. An incubation apparatus, comprising:

a removable base segment;

a reservoir residing on the removable base segment, the reservoir having a first chamber and a second chamber separated by a gas permeable, hydrophobic membrane such that the membrane forms a water-tight seal between the first chamber and the second chamber;

a cell growth container residing on the removable base segment, the cell growth container having a chamber for growing cells, the cell growth container further having at least one transparent surface allowing viewing of cells within the chamber through the transparent surface, wherein the cell growth container is gas tight except for paths that permit media from the reservoir to enter and exit the cell growth container so that introduction of gas to the cell growth container is prevented except for the media;

a pump external to the removable base segment, the pump coupled to the cell growth container and the reservoir such that the media is pumped from the second chamber of the reservoir to the chamber of the cell growth container; and a mixer external to the removable base segment, the mixer having a plurality of gas containers coupled to a plurality of valves, respectively, the plurality of gas containers including at least a first gas container containing a first gas and a second gas container containing a second gas, the plurality of valves including at least a first valve coupled to the first gas container and a second valve coupled to the second gas container;

a first temperature control element;

a first temperature sensor residing on the removable base segment; and control logic configured to automatically control the first and second valves such that a desired ratio of at least the first gas and the second gas is mixed by the mixer thereby forming a gas mixture, the control logic further configured to automatically control the first temperature control element based on the first temperature sensor such that the media is heated by the first temperature control element to a specified temperature range, wherein the mixer is coupled to the reservoir such that the gas mixture from the mixer enters the first chamber of the reservoir, passes through the membrane, and diffuses into the media in the second chamber of the reservoir.

2. The apparatus of claim 1, wherein the reservoir has a hole extending to the first chamber such that gas within the first chamber can vent from the first chamber.

3. The apparatus of claim 1, wherein the first temperature control element and the first temperature sensor are mounted on the reservoir.

4. The apparatus of claim 1, wherein the first temperature control element and the first temperature sensor are mounted on the container.

5. The apparatus of claim 4, further comprising a second temperature control element mounted on the reservoir.

6. The apparatus of claim 5, further comprising a second temperature sensor mounted on the reservoir, wherein the control logic is configured to control the second temperature control element based on the second temperature sensor, and wherein heat emitted by the second temperature control element affects a temperature of media within the chamber of the cell growth container.

7. The apparatus of claim 1, further comprising an air pump coupled to the mixer, wherein the mixer is configured to mix at least the first gas and the second gas with air from the air pump such that the gas mixture comprises the air from the air pump.

8. The apparatus of claim 1, wherein the cell growth container has a first channel and a second channel, and wherein the second channel has a plurality of mouths to the chamber of the cell growth container.

9. The apparatus of claim 8, wherein at least two of the mouths are aligned.

10. The apparatus of claim 1, wherein the cell growth container has a support member, a first channel, a second channel, a first plate, and a second plate, wherein the first and second plates are separated by the support member, and wherein the first and second channels pass through the support member.

11. The apparatus of claim 10, wherein at least a portion of the first plate is transparent.

12. The apparatus of claim 11, wherein at least a portion of the second plate is transparent.

13. The apparatus of claim 12, wherein the base has a hole and the portion of the second plate is exposed by the hole.

14. The apparatus of claim 12, wherein the second channel has a plurality of mouths to the chamber of the container.

15. The apparatus of claim 14, wherein at least two of the mouths are aligned.

16. The apparatus of claim 15, wherein the gas permeable membrane is composed of polytetrafluoroethylene.

17. The apparatus of claim 16, wherein a pore size of the gas permeable membrane is 0.2 microns.

18. The apparatus of claim 1, wherein the reservoir and container are integrated.

19. A method, comprising the steps of:

providing an incubation apparatus having a pump and a mixer; inserting a removable base segment into the incubation apparatus, the removable base segment having a reservoir and a cell growth container, wherein the reservoir has a gas permeable, hydrophobic membrane separating a first chamber of the reservoir from a second chamber of the reservoir and forming a water-tight seal between the first chamber and the second chamber, and wherein the cell growth container has at least one transparent surface;

injecting cells into the container, wherein the cell growth container is gas tight except for paths that permit the media from the reservoir to enter and exit the cell growth container so that introduction of gas to the cell growth container is prevented except for the media;

pumping the media from the second chamber of the reservoir into the cell growth container via the pump;

automatically controlling a plurality of valves respectively coupled to a plurality of gas containers such that at least a first gas from one of the gas containers mixes with a second gas from another of the gas containers thereby forming a gas mixture comprising a desired ratio of at least the first gas and the second gas;

causing the gas mixture to pass from the first chamber of the reservoir through the membrane to the second chamber of the reservoir such that the gas mixture diffuses with the media in the second chamber of the reservoir;

automatically heating the media based on a temperature sensor residing on the removable base segment; and removing the removable base segment from the incubation apparatus.

20. The apparatus of claim 1, wherein the reservoir is external to the cell growth container and coupled to the cell growth container via a hose, and wherein the media passes through the hose while traveling from the second chamber of the reservoir to the chamber of the cell growth container.

21. The apparatus of claim 1, wherein the first temperature sensor is for sensing a temperature of the media in the reservoir, wherein the apparatus further comprises a second temperature sensor for sensing a temperature of the media in the cell growth container.

22. The apparatus of claim 1, further comprising:

a frame; and a microscope mounted on the frame, wherein the removable base segment is positioned on the frame such that the cells in the cell growth container are viewable to the microscope through the transparent surface.

23. The apparatus of claim 1, wherein the cell growth container has a wall having a channel for passing the media into the chamber of the cell growth container, wherein the reservoir is coupled to the cell growth container via a hose, the hose extending from the reservoir to the channel.

* * * * *